United States Patent [19]

Micco

[11] Patent Number: 4,819,652
[45] Date of Patent: Apr. 11, 1989

[54] C W AND PULSE DOPPLER DIAGNOSTIC SYSTEM

[75] Inventor: Alexander J. Micco, Lakewood, Colo.

[73] Assignee: University Patents, Inc., Westport, Conn.

[21] Appl. No.: 699,676

[22] Filed: Feb. 8, 1985

[51] Int. Cl.[4] .............................................. A61B 10/00
[52] U.S. Cl. ............................. 128/661.09; 73/861.25
[58] Field of Search ............................... 128/660–663; 73/861.25

[56] References Cited

U.S. PATENT DOCUMENTS

| 4,318,413 | 3/1982 | Iinuma et al. | 128/660 |
| 4,407,293 | 10/1983 | Suarez, Jr. et al. | 128/660 |
| 4,476,874 | 10/1984 | Toenzer et al. | 128/663 |
| 4,540,946 | 9/1985 | Sainz et al. | 128/663 |
| 4,563,899 | 1/1986 | Nakamura | 128/663 X |
| 4,582,067 | 4/1986 | Silverstein et al. | 128/663 |

OTHER PUBLICATIONS

Von Hock, A. P. G., "On the Development of a Multi--Gate Pulsed Doppler System with Serial Data Processing", University of Limburg, Presented 5 Mar. 1982, pp. 19–20, 33–35.
Wells, P. N. T., "Biomedical Ultrasonics", Academic Press, London, ©1977, pp. 356–357.
Grof, R. F., "Modern Dictionary of Electronics", Howard W. Sons & Co., Indianapolis, Ind., ©1970, p. 109.

Primary Examiner—Francis J. Jaworski
Attorney, Agent, or Firm—Rosen, Dainow & Jacobs

[57] ABSTRACT

In an interlaced pulse-echo and range-gated Doppler system, an ultrasound transmitter generates a train of constant repetition rate echo pulse interlaced with a Doppler pulse train of plural bursts. The time duration between each burst and the preceding range gate opening is held constant while the time to the successive range gate opening is automatically varied to provide a continuously variable PRF tracking of the console range gate depth setting. The power of the transmitted signal is internally varied in the same sense and the cutoff frequency of the receiver low pass tracking filters is varied in the opposite sense to optimize signal-to-noise ratio at various tissue inspection depths. Selectable turnable high pass filters normalized to low velocity roll-off eliminate artifact for peripheral or central vascular probes. The detection system operates in quadrature and includes a synchronous demodulator and a peak detector, and a level detector operative on peak detected signals. Transducer probes interchangeably usable in the system include within each probe a narrow band amplifier critically turned to the respective probe crystal to provide further S/N ratio improvement. The system is operable in CW or pulsed Doppler modes dependent on switch setting on the split crystal probe.

23 Claims, 15 Drawing Sheets

C W AND PULSE DOPPLER DIAGNOSTIC SYSTEM

BACKGROUND OF THE INVENTION

This invention relates to pulse Doppler diagnostic systems, and is more particularly directed to improvements in such systems enabling increased accuracy, facility of use, signal-to-noise ratio, and adaptability to different modes of operation of such systems. While the following disclosure is directed specifically to the use of the invention in medical applications such as monitoring blood flow, it will be apparent that the concepts of the invention are adaptable for other applications, and it is intended herein that the scope of the invention include such other applications.

In the past, medical systems have been provided that employ pulse Doppler ultrasound for non-invasive cardiac diagnosis, such as monitoring of blood flow in vessels and arteries and determining pulmonary arterial pressure or hypertension. Such systems employ echo, continuous wave or pulse Doppler ultrasound signals. Such systems are disclosed, for example, in U.S. Pat. No. 4,058,001, Waxman, U.S. Pat. No. 4,137,777, Haverl, U.S. Pat. No. 4,205,555, Hashiguichi, U.S. Pat. No. 4,242,911, Martin, U.S. Pat. No. 4,103,679, Aronson, U.S. Pat. No. 4,141,347, Green et al., U.S. Pat. No. 3,802,253, Lee, U.S. Pat. No. 4,097,835, Green, U.S. Pat. No. 4,313,444, Glenn, U.S. Pat. No. 4,318,413, Iinuma, U.S. Pat. No. 4,387,720, Miller, U.S. Pat. No. 4,390,025, Takemura, et al, U.S. Pat. No. 4,398,540, Takemura et al and U.S. Pat. No. 4,407,293, Suarez, Jr., et al.

Using the Doppler principle, pulse and continuous wave ultrasound are presently being used in medicine to make non invasive measurements of peripheral and central cardiovascular blood flow velocities. Other ultrasound measurements such as cardiac valve movement velocities, valve time intervals, and contractual and relaxation periods of the cardiac chambers provide useful diagnostic information in the assessment of cardiovascular disease. The velocity measurements are made by processing the returned "echo" signals for a change in frequency. This Doppler-shifted frequency, which is directly related to the velocity of the reflector, is usually in the audible range and contains useful diagnostic information simply by listening. However, if the velocity and its direction are to be known and recorded, further electrical processing is necessary.

Flow velocity and direction information can be obtained by comparing the received signal frequency with the transmitted frequency and the transmitted frequency shifted 90 degrees in phase. Using tis technique, two Doppler shift signals are obtained which are equal in frequency but different in phase by 90 degrees according to velocity direction. These signals are commonly referred to as quadrature audio. When presented to the quadrature audio demodulator, if, for instance, the first channel is leading the second channel by 90 degrees, i.e., flow "toward the probe", the analog voltage at the output would be a positive value linearly related to the Doppler frequency. If, on the other hand, flow is away from the probe, the phase relationship will be reversed and the analog voltage at the output would have negative value in relation to frequency.

In the past, Doppler-shifted audio signals have been processed for visual inspection by fast Fourier transforms, Kay sonograms and direct frequency-to-voltage conversion by "zero crossing rate meter". All of these techniques have their strong and weak points. The zero crossing rate meter is simply a low-cost frequency-to-voltage converter, wherein the conversion is made by integrating pulses of constant amplitude and width which are generated when the Doppler frequency signal crosses a zero voltage reference.

Three common faults of the zero crossing rate meter are as follows: (1) false counts can occur when noise is present, which may cause extra crossings, (2) counts can be missed if a low frequency component is present, allowing the higher frequencies to ride above or below the zero level (riding high syndrome), (3) unpredictable phase shift between the quadrature channels can occur resulting in a loss of flow direction information. These conditions are the rule rather than the exception when processing back- scattered signals from deep vessels. The introduction of hysteresis and filters into the circuit may lessen the noise problems but introduce phase errors that degrade the important direction determination.

BRIEF STATEMENT OF THE INVENTION

The present invention is directed to a method and apparatus for improving pulse Doppler diagnostic systems, and overcoming the above problems of the known arrangements.

In accordance with one embodiment of the invention, in order to improve the ability of the operator to locate targets, the concepts of echo pulse transmission and pulse Doppler transmission are combined, with echo pulse receiving times being interlaced with pulse Doppler signals. With this arrangement, the time interval between echo pulses preferably (although not necessarily remains constant, with the pulse repetition rate of the Doppler pulse bursts, within a given cycle, being variable if desired. The advantages of Doppler pulse diagnosis are hence retained, while enabling a "look ahead" feature by the use of the echo pulses.

In a further embodiment of the invention, the transmitted power of the ultrasound pulses for pulse Doppler measurements is controlled to automatically track the range gate depth setting. This feature increases the signal-to-noise ratio for all range gate depths by optimizing transmitted power for a given depth.

In a still further feature of the invention, the Doppler pulse repetition rate is controlled to vary inversely with the range gate depth setting. As a consequence, the effective data sampling rate is maximized.

In a still further feature of the invention, the received Doppler pulse signals are passed through two tunable filters. (1) A high frequency cutoff filter for decreasing the cutoff frequency automatically as the range gate depth increases. In addition, this high frequency cutoff filter removes the Doppler repetition rate frequency, while preserving all frequencies which carry valid velocity information. (2) A tunable low frequency cutoff filter is also used to remove low frequency signals relating to very slow velocities of no interest such as vessel or cardiac wall motion. The low frequency roll off is normalized automatically (in this system) to velocity as probes of differing frequencies are selected by the operator. The operator may select a low velocity roll off such as 0.05 meters/sec for peripheral vascular and 0.1 meters/sec for central cardiovascular examination. This arrangement further increases the signal-to-noise ratio of the system.

In a still further feature of the invention, separate probes are provided for separate measurement frequencies, preferably in the range of 1-7 MHz. The separate probes each have narrow band amplifiers with their impedances critically tuned to the probe crystal to minimize Johnson noise and to provide the maximal signal-to-noise ratio obtainable at the specific frequency.

In a still further feature of the invention, a full wave quadrature audio demodulator is provided for detecting the voltage maxima and minima, as an economical means for obtaining a mean velocity signal. The demodulator preserves the phase relationship and the magnitude of the velocity and, unlike conventional zero-crossover detectors, is insensitive to base line voltage shifts and low frequency noise.

In accordance with the invention it is recognized that zero crossing rate meters require a signal-to-noise ratio greater than 10 for reasonable accuracy.

Yet another feature of this invention is the capability of using the instrument in the continuous Doppler mode as well as in the pulsed Doppler mode. The mode may be selected by a switch on a split crystal probe. The same low noise impedance matching network and amplifier are used.

BRIEF FIGURE DESCRIPTION

In order that the invention will be more clearly understood, it will now be disclosed in greater detail with reference to the accompanying drawings wherein:

FIG. 17b illustrates a modification of the circuit of FIG. 17a;

DISCLOSURE OF PREFERRED EMBODIMENT

Figure 1:
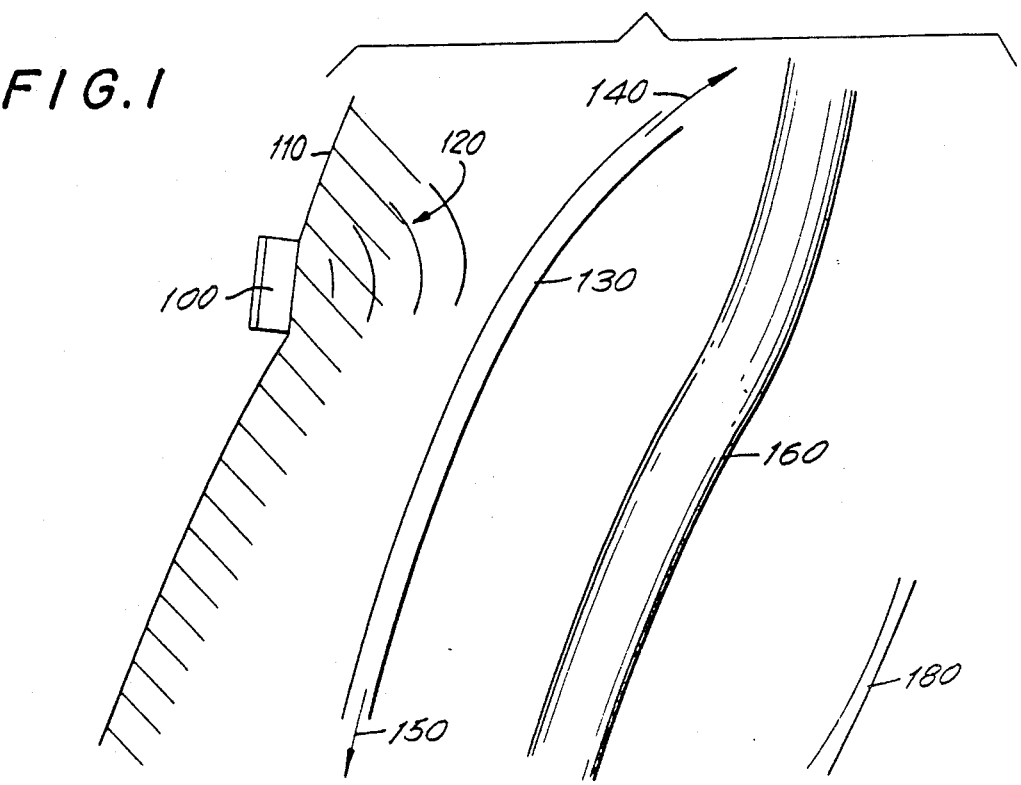
FIG. 1 is an illustration of the use of an ultrasound transducer determining the velocity of blood in various vessels.
Figure 2:
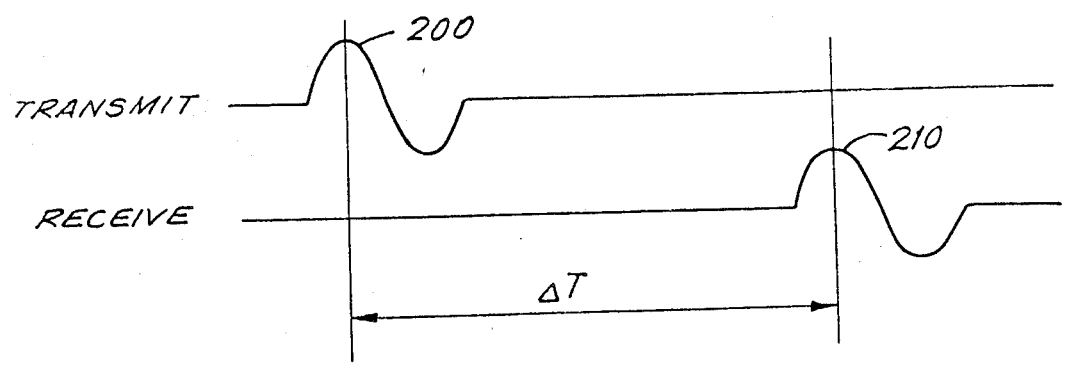
FIG. 2 illustrates the principle of echo pulse transmission systems.

The present invention relates primarily to a "pulsed Doppler" system although it may employ "continuous wave Doppler" and "echo" systems. FIG. 1 illustrates an ultrasound transducer 100 which is capable of both transmitting and receiving ultrasound pulses. The transducer 100 is placed against the surface of the skin 110 (or other body of the object to be examined), and directs ultrasonic signals 120 at blood vessels 130, 160 and 180. The blood in the vessel 130, for example, may be moving in the direction of arrow 140 or in the direction of arrow 150. Using echo technology, a single ultrasonic pulse 200 is transmitted as shown in FIG. 2. In this instance the blood vessel 130 reflects the ultrasonic pulse 200 and the transducer receives the reflected pulse 210 after a delay in time ΔT has occurred.

Figure 3:
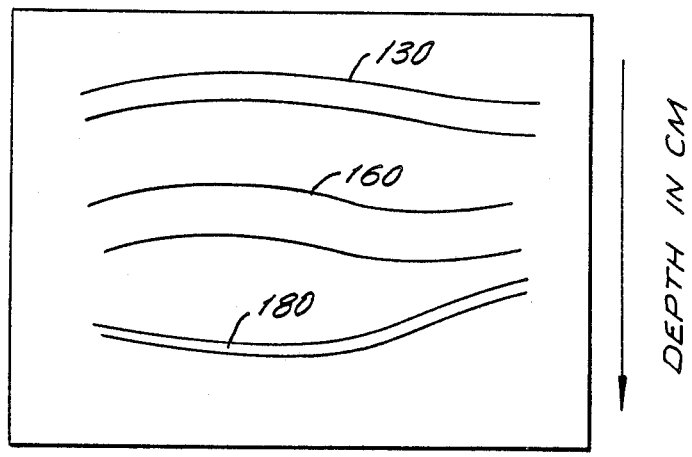
FIG. 3 illustrates vessels at various depths in a tissue.

Conventionally the received echo pulses reflected from vessels and tissue strata are processed and can be displayed on a monitor scope such as that depicted in FIG. 3. Typically measurements can be made directly from the display as to vessel diameter, wall thickness, heart valve movement, etc.

Figure 4:
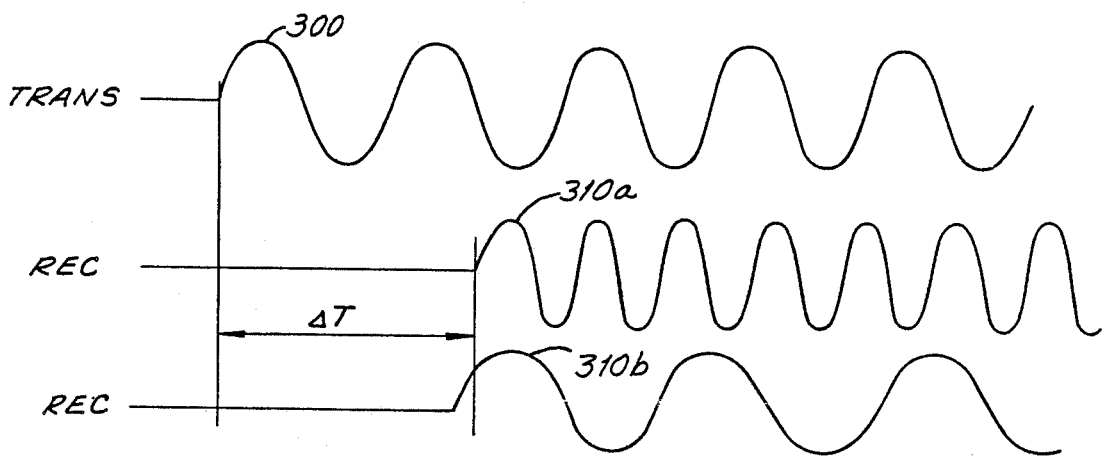
FIG. 4 illustrates the principle of continuous wave ultrasound diagnostic systems.

According to continuous wave Doppler technology, the transmitted continuous wave signal 300 is shown in FIG. 4. Upon hitting the blood flowing in blood vessel 130, the continuous wave of cycles 300 are reflected back and are received as reflected cycles 310a or 310b. Cycles 310a are reflected pulses of higher frequency, indicating that the blood is flowing in the direction of arrow 150, and reflected pulses 310b are of lower frequency, indicating that the blood is flowing in the direction of arrow 140. By determining the difference in frequencies between the transmitted frequency 300 and the received frequency 310, not only can the direction of the blood be ascertained but the difference in frequency is proportional to the velocity of the blood.

Figure 5:
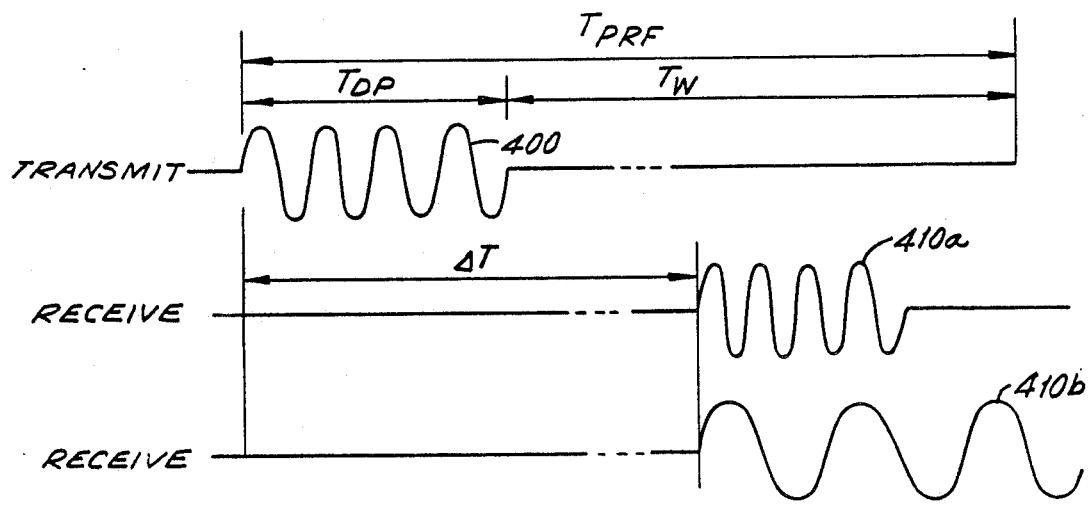
FIG. 5 illustrates the principle of pulse Doppler diagnostic systems.

A pulsed Doppler technique, shown in FIG. 5, utilizes a pulsed wave form 400 occurring at periodical intervals. After a delayed time period ΔT, the reflected cycles 410a (or 410b) are received by the transmit/receive crystal 100. Again, the frequency of the reflected pulse 410 determines both the direction and the flow velocity of the blood in vessel 130.

Typically pulse 400 consists of a burst of 4 or 8 cycles of the transmit frequency. In either the continuous wave or pulsed Doppler technique the transmit signal 300 or 400 will reach all three vessels 130, 160, and 180, shown in FIG. 1, in its path and Doppler-shifted signals 410a or 410b will be received from all three vessels. The receiver in continuous wave Doppler systems has no way to discriminate between the signals reflected from the three vessels and will, unfortunately, give a mean flow velocity of the blood flowing in all three vessels. On the other hand, in the pulsed Doppler system the cycles 410 reflected from vessel 130 will be received at the crystal 100 at a time ΔT later than the transmit burst 400. By applying a time gating technique (commonly known as range gate) to the receiver, to be discussed later, only the signals received from vessel 130 will be amplified and processed for determining blood flow velocity and direction. If so desired, the range gate may be moved to precisely measure the velocity and direction of the blood flowing in vessels 160 or 180.

While the present invention is primarily directed to the providing of an improved system using the pulsed Doppler and continuous wave techniques of the type shown in FIGS. 4 and 5, in accordance with one embodiment, to be now discussed, an echo pulse is interlaced with the pulsed Doppler bursts.

ECHO PULSES INTERLACED WITH PULSED DOPPLER BURSTS

Figure 6:
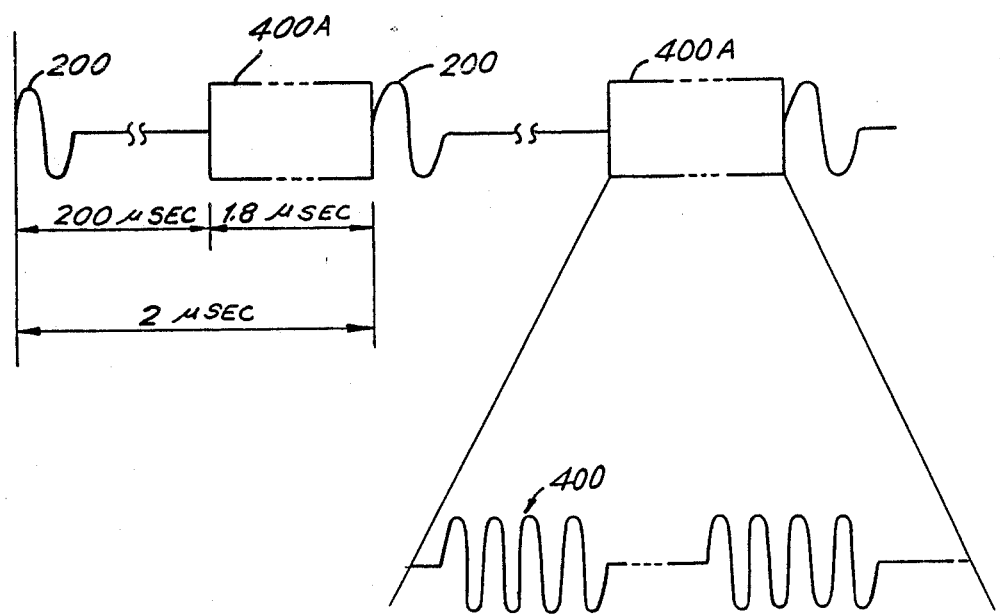
FIG. 6 illustrates the principle of the combined echo pulse and pulse Doppler diagnostic system in accordance with the invention.

As shown in FIG. 6, one embodiment of the present invention interlaces the conventional echo pulse of FIG. 2 with the Doppler pulses of FIG. 5. The echo frame of, for example only, 200 microseconds for the echo pulse is constant. Two hundred microseconds is sufficient time for an ultrasonic pulse to travel 15 cm into human tissue (the practical maximum depth of penetration). This serves a very useful function which will be explained by reference back to FIG. 1. In FIG. 1 deeper blood vessels 160 and 180 are present. In accordance with the techniques of the present invention, as shown in FIG. 6, the system of the present invention can measure the blood flow in blood vessel 130 based upon the sequences of pulses 400A of pulsed Doppler signals 400.

As will be subsequently explained, the pulse repetition frequency (PRF) of the pulsed Doppler signal 400 can be tuned precisely to allow the measurement of the blood flowing in vessel 130. Because of this precise setting of the PRF, the Doppler pulses of the deeper vessels 160 and 180 will not be received. By interlacing the echo pulse 200 with the pulsed Doppler signal, and allowing the fixed time period of 200 microseconds, signals may be received from greater depths and the signals from vessels 160 and 180 will be present and displayed on the monitor scope shown in FIG. 3. It is important to note that the echo pulse is a single cycle of the transmit frequency, thus providing the maximum resolution to the echo signal to be displayed. Hence, the interlaced echo pulse 200 provides "look ahead" information which aids in the use of the system of the present invention. For example, an operator of the present invention can quickly tune the pulsed Doppler signal 400 on any one of several blood vessels, based upon the "look ahead" information provided by the echo pulse.

In the same manner this arrangement allows the operator to more precisely place the range gate in the center of the vessel or chamber in which the blood velocity is to be measured. The echo signals and the reflected Doppler signals are separately processed by the system of the present invention.

In the preferred embodiment of the present invention, as indicated in FIG. 6, the generation of the echo pulses 200 is approximately a 500 Hz signal whereas, the generation of the pulsed Doppler signals, PRF of the bursts, is continuously variable from 24,000 Hz to 5,000 Hz. The echo transmission is synchronized with the Doppler transmission and the echo pulse is of fixed amplitude in a fixed time frame. As will be explained, the Doppler pulse time frame is variable and the amplitude is also variable.

CONTINUOUS MODIFICATION OF THE PRF SIGNAL

This embodiment of the invention is directed to the modification of the PRF of the pulsed Doppler signals, which may be employed with or without the above-disclosed interlacing with echo pulse signals. The range of 1-7 MHz for the Doppler frequency is the preferred frequency range for the Doppler pulses 400 shown in FIG. 5. The higher the transmit frequency, the greater the shift in frequency because of the Doppler effect on the reflected signal. This, of course, enables greater resolution in determining the velocity of the blood. The high frequency (e.g., 7 MHz) is especially suited for examining smaller vessels such as those found in children. However, the lower the frequency the better the ability of the ultrasound to travel through human tissue. Hence, lower frequencies (e.g., 1 MHz) are used to measure the flow of blood in deeper tissues.

Another matter of great importance in the pulsed Doppler technique is the phenomenon of "signal aliasing." Using the pulsed Doppler technique, the Doppler-shifted signal returned from vessel 130, for example, is sampled only once in each transmit frame $T_{PRF}$. As predicted by the sample theorem the maximum detectable Doppler-shifted frequency can be no greater than one half the sample rate, which is the same as the transmit repetition rate (PRF). If the Doppler-shifted frequency exceeds one half the PRF, "aliasing" will occur and the signal represents the blood flow velocity in a useless manner. The first step conventionally to take when aliasing might occur is to sacrifice the higher resolution obtained from a higher frequency transducer and move to a lower transmit frequency, e.g., 1 MHz. In accordance with the present invention the highest PRF is maintained for all measurements regardless of depth and regardless of probe frequency. This is achieved in this invention by providing a continuously variable PRF, the PRF being determined by the depth setting of the sample gate. In other words, a continuously variable PRF that tracks the sample gate, i.e., the transmit burst 400, is initiated almost instantly upon completion of taking a sample at any depth.

The present invention, therefore, tailors the pulse repetition frequency (PRF) to the depth of the blood vessel being examined. The PRF is the frequency at which the Doppler pulses are transmitted, which in FIG. 5 has a period of $T_{PRF}$. The period of $T_{PRF}$ contains preferably four cycles at the desired frequency between 1 to 7 MHz occurring in time $T_{DP}$, and a window of time $T_w$ in which the receiver 100 receives reflected pulses.

The invention thus provides a pulsed Doppler signal 400 which has its PRF continuously variable so that it can be set at precisely the depth of the blood vessel to be analyzed, and further provides a narrow band gate, commonly known as the sample volume, to gate the reflected Doppler signal into the receiver only from that depth. Hence, the present invention utilizes a depth control circuit which effects a re-transmission of cycles 400 at the end of the sample periods, thus effecting the maximum obtainable PRF, while examining the blood flow from a vessel at that depth.

Figure 11:
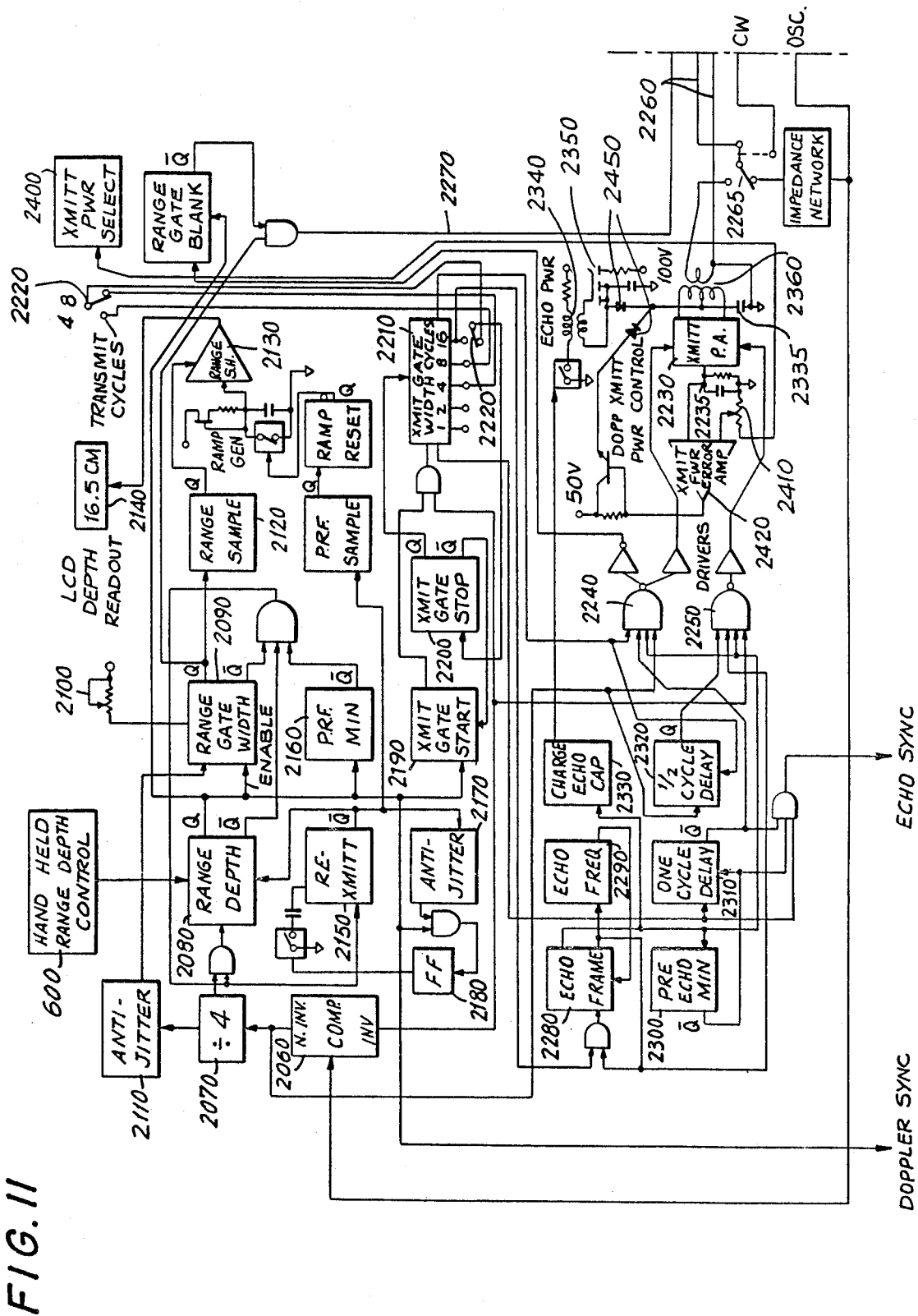
FIG. 11 is block diagram illustrating the transmission and timing circuits of an ultrasound diagnostic system in accordance with the invention.

The control 600 shown in FIG. 11 can thus, for example, be continuously adjusted to examine a blood vessel between 0.5 and 17 cm deep in human tissue. The control 600 simultaneously adjusts the range gate (i.e., the time delay between the pulsed Doppler transmit burst and the received signal gated to the receiver and the PRF, since the succeeding pulsed Doppler burst is transmitted with a fixed delay following the range gate.

Figure 7:
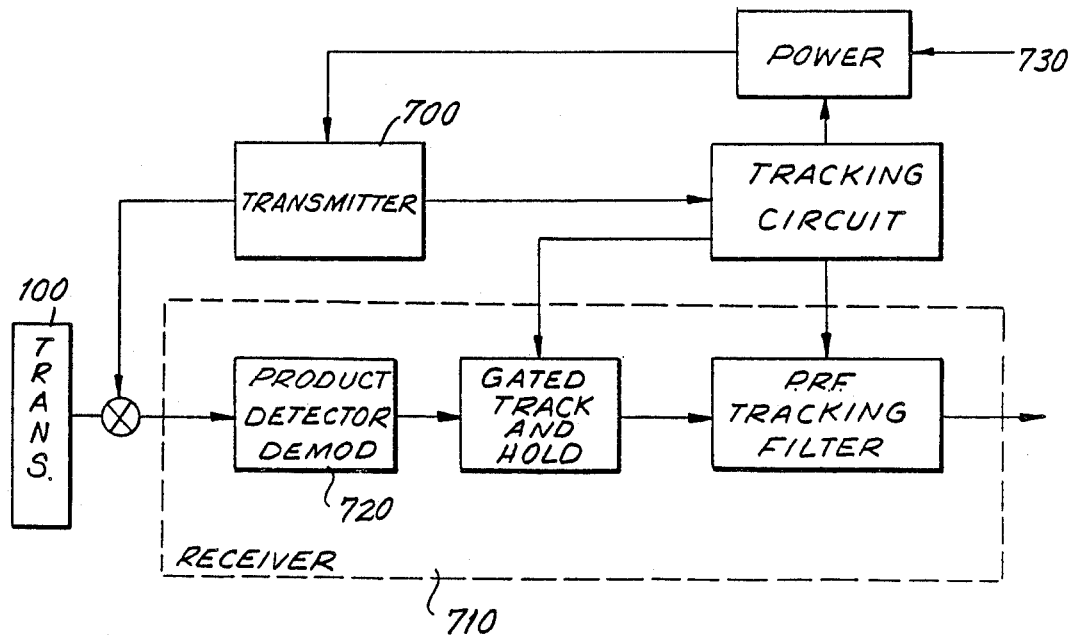
FIG. 7 is a block diagram illustrating a Doppler pulse transmission system in accordance with the invention, wherein the power of the pulses is controlled as a function of depth.

The operation of the depth setting feature of the invention will now be discussed. In FIG. 7, the transducer 100 receives transmitted pulses from circuit 700 and, in turn, delivers received pulses to receiver 710. A demodulator 720 compares the received pulses with the transmitted pulses to output a difference signal relating to the Doppler shift. With reference back to FIG. 1, Doppler signals are reflected from the shallow blood vessel 130 as well as from the deeper blood vessels 160 and 180.

Figure 8:
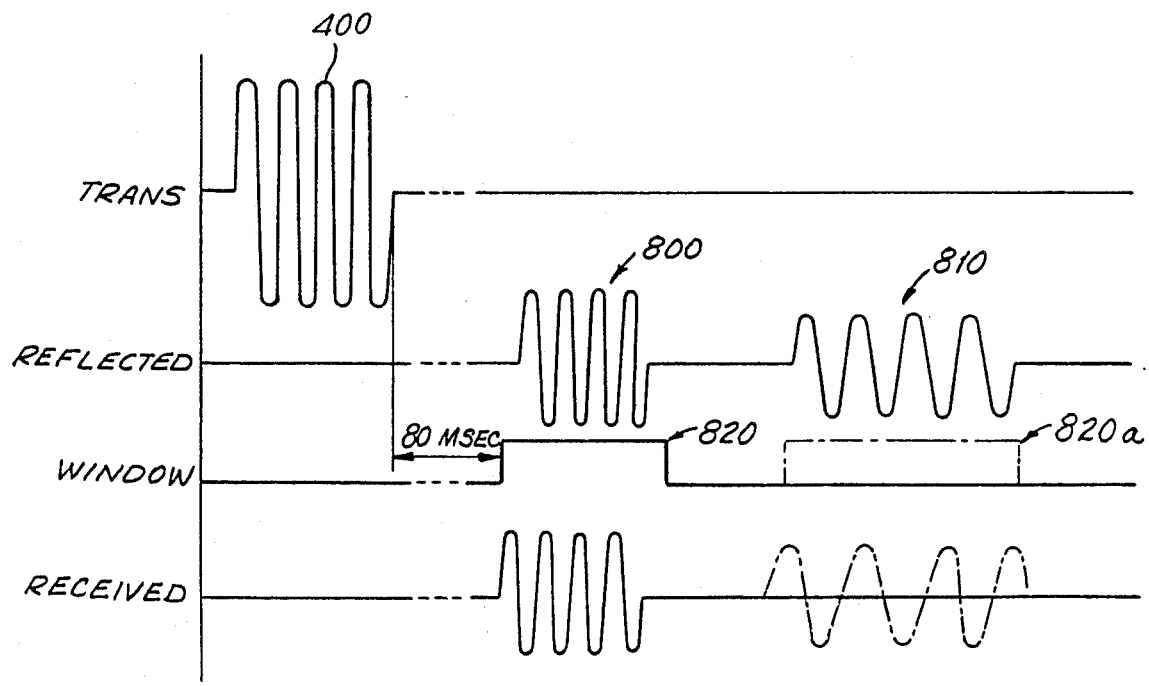
FIG. 8 illustrates the use of range gates in a pulse Doppler diagnostic system.

FIG. 8 shows the transmitted pulse 400 as well as the reflected pulses 800 from the first blood vessel 130 and the reflected pulse 810 from the deeper blood vessel 160. The present invention, by providing the above-described variable control is capable of selectively receiving the reflected pulses 800 or 810 by adjustment of a "range gate" window 820 to only receive reflected pulses from a desired depth. For example, assume that blood vessel 130 of FIG. 1 is to be analyzed. This is a shallow blood vessel and, therefore, a high frequency Doppler pulse, closer to 7 MHz, is desired. According to the present invention, as will be subsequently explained, a higher frequency is delivered by transducer 100 into the tissue and the control 600 is set for the proper shallow depth, for example, 3 cm deep. Because it is known that ultrasound is delayed approximately 13.6 microseconds per centimeter of distance to the reflector, a "range gate" window 820 is set approximately 80 microseconds after the transmission of the Doppler pulses to receive only the reflected Doppler pulses 800 from vessel 130.

This window, as shown in FIG. 8, is termed the range gate 820. The characteristics of the range gate need to be discussed. First, the position of the range gate can be adjusted by setting the control 600 to any position in time $T_w$ of FIG. 5, which corresponds to the desired depth. Hence, should the reflected Doppler signal from blood vessel 160 be analyzed, the range gate 820 can be shifted in time (or depth) to the location shown in dotted lines as 820A, which then would analyze only the received pulses also shown in dotted lines. In other words, the range gate 820 is selectively adjustable in time (or in depth) to receive only reflected pulses from desired blood vessels.

Figure 9A:
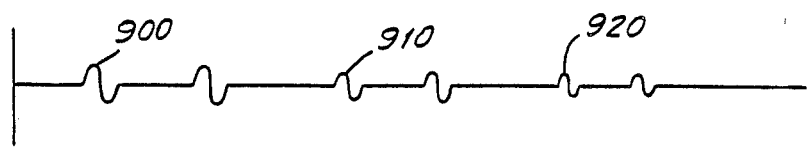
FIGS. 9a-9d illustrate the relative reception of pulses in echo and pulse Doppler systems.
Figure 9B:
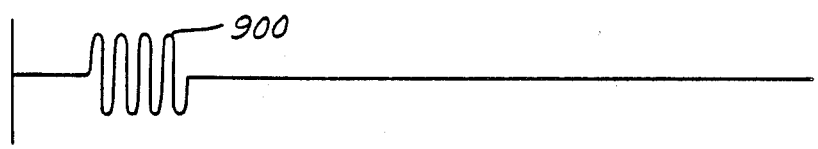
Figure 9C:
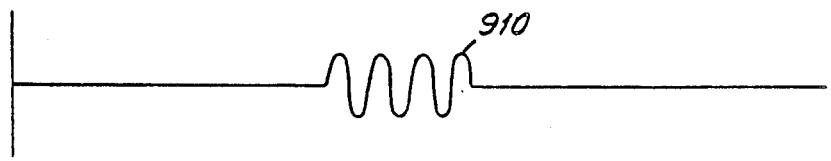
Figure 9D:
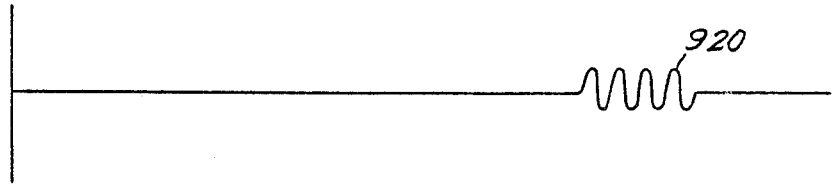

The interrelationship between the interlaced echo pulse and the transmitted pulsed Doppler signals, as shown in FIG. 6, will now be discussed with reference to FIG. 9. The generation of the echo pulse 200 results in a received trace in FIG. 9a of three blood vessels, with pulse 900 corresponding to the echo pulse from blood vessel 130, pulse 910 corresponding to the reflected pulse from blood vessel 160, and pulse 920 corresponding to the reflected pulse from blood vessel 180. The window 820 can be moved by adjusting control 600 to various depths corresponding to the depths of each of these blood vessels. Hence, FIG. 9b shows the Doppler signal reflected from blood vessel 130 on the echo pulse display, with the window set for the depth of vessel 130. When the window is moved deeper to analyze the reflected Doppler pulses from blood vessel 160, the Doppler signals shown in FIG. 9c are reflected from blood vessel 160. And finally, FIG. 9d shows the reflected Doppler signal when the range gate is set for the deepest blood vessel 180. It is important to note that the amplitudes of the deeper-reflected ultrasonic pulses are lower. (FIGS. 9b–9d do not necessarily depict an actual display.)

Figure 9E:
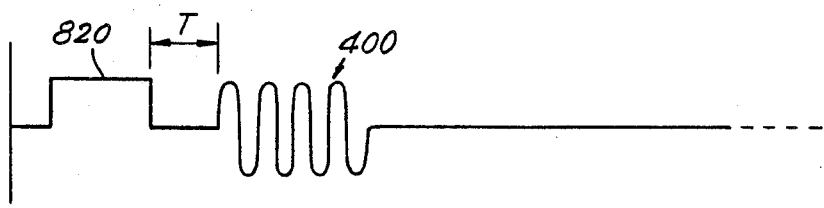
FIGS. 9e-9g illustrate the variation of pulse repetition frequency, as a function of depth, in accordance with the invention.
Figure 9F:
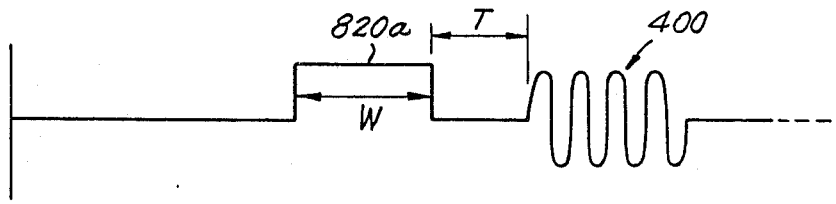
Figure 9G:
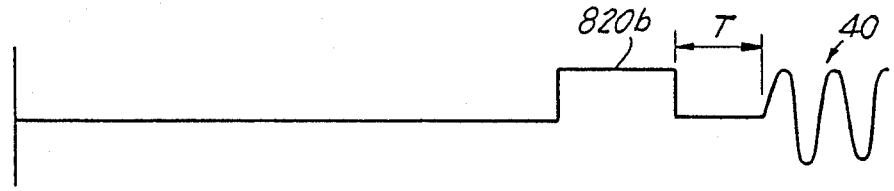

In analyzing FIGS. 9a–9d it can be observed that there is no reason to ever receive any additional reflected Doppler signals from deeper-located blood vessels since the setting of the range gate determines the desired depth. Therefore, as shown in FIGS. 9e, 9f, and 9g (which show only the reflected Doppler signals), the Doppler pulse 400 is retransmitted at a fixed time T after the range gate setting. Hence, adjusting the control 600 to different depths, tailors the retransmission of the pulsed Doppler signal 400 to occur a fixed time after the generation of the range gate. This feature in accordance with the invention continuously varies the PRF of the system. This is further explained with reference to FIG. 5, where $T_w$ is the overall window of time from transmission to retransmission of pulses 400. $T_w$ is variable since retransmission occurs immediately (i.e., T) after the range gate setting. Thus, for example, for a depth setting of 2 cm, 66 bursts of pulses 400 are transmitted in the 1.8 msec time span shown in FIG. 6, whereas for a depth setting of 7 cm only 20 bursts of pulses are transmitted in the same time. Hence, the pulse repetition frequency is variable in accordance with the range gate depth setting even when operating in the interlaced mode.

In other words, the system in accordance with the invention receives all of the "look ahead" echo pulses interlaced with the Doppler pulses, but ignores all reflected Doppler pulses from vessels deeper than the one being analyzed, and immediately retransmits the Doppler signal at a fixed time T later. The transmission of the pulsed Doppler signal thus tracks the range gate. FIG. 9e corresponds to the situation in FIG. 9b, FIG. 9f corresponds to the situation in FIG. 9c, and FIG. 9g corresponds to the situation depicted in FIG. 9d.

In addition, the width W of the range gate can be selectively adjusted. The changing of the width W of the range gate does not affect the retransmission time T.

While the time T is fixed at depths greater than 3 cm, at depths less than 3 cm the reflected signals from the surrounding blood vessels or tissue overlap the transmitted signals, thereby destroying range resolution. Therefore, at depths less than 3 cm the range gate window can be selectively adjusted to shallow depths, however, in accordance with a further feature of the invention, the retransmission will not occur until approximately 40 microseconds to eliminate the overlapping of signals.

The above-disclosed system of the invention, by means of a depth control, is capable of tuning in or receiving only the reflected Doppler signals from blood vessels at a desired depth by selectively adjusting the range gate. The retransmission of the pulsed Doppler signal occurs a fixed time after the setting of the range gate so that the PRF is continuously varied as a function of the depth of the vessel. This increases the accuracy and the resolution of the reading while reducing the probability of aliasing. At depths less than 3 cm, however, the retransmission of the signal occurs at a fixed PRF even though the range gate can be selectively adjusted to tune in blood vessels shallower than 3 cm.

MINIMIZATION OF ELECTRICAL NOISE

According to a further feature of the invention, several separate probes are utilized. Each of these probes is designed to transmit and receive at a specific frequency, for example:

Probe 0—1 MHz
Probe 1—2 MHz
Probe 2—3.25 MHz
Probe 3—5 MHz
Probe 4—7 MHz

Figure 10:
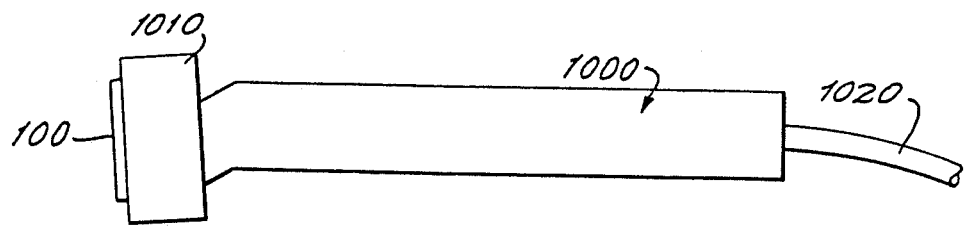
FIG. 10 is a diagrammatic illustration of a transducer.

Each of these probes, as shown in FIG. 10, contains a narrow band amplifier 1000, a swivel head 1010 carrying transducer 100 and an electrical cable 1020. In accordance with the invention, the first stage of the receiving amplifier 1000 is in the probe. This first stage is a narrow band amplifier with a fixed gain. The narrow band amplifier is designed to receive signals at its optimum electrical signal-to-noise ratio. The power of the transmitted signal (wave form 400 of FIG. 6) is then adjusted to accommodate the depth of the vessel being analyzed. It is recognized that attenuation of an ultrasound signal increases as the square of the distance involved. Hence, in adjusting the depth control 600, as shown in FIG. 7, the power 730 delivered to the transmitter 700 is increased according to the depth of the blood vessel being analyzed: the greater the depth, the greater the power.

Hence the transmit power delivered to the crystal for Doppler pulses 400 is continuously variable and automatically adjusts to the depth to be penetrated as control 600 is adjusted. Attenuation in human tissue of the transmitted Doppler frequency 400 increases as the transmit frequency is increased. Therefore, as the transmit frequency 400 is increased, the transmit power is also increased automatically to compensate for attenuation. This is contrary to prior devices where the power is fixed at a constant value while the range gate is moved to different depths, and transmit frequencies are changed. Some known approaches do, in fact, have a separate operator control for manually adjusting the power level. Such controls do not automatically track the range gate setting as specifically done in accordance with the present invention.

This is an extremely important feature of the present invention. By designing several separate probes each having a narrow band amplifier at its optimum signal-to-noise ratio configuration contained therein and then automatically modifying the transmitter power to increase the power for greater depths of penetration, extremely high signal-to-noise ratios are obtained.

Doppler signal processing becomes complicated by the fact that signal levels reflected from solid structures such as walls and valves are orders of magnitude greater than reflections from red cells. The stronger signals have a tendency to saturate the receive electronics and mask the desired Doppler signals. This is especially true in conventional systems where the transmit power is held constant, near the maximum of 100 mW/cm$^2$ crystal area. Even the best damped crystal will have a longer ringing time and generate spurious reflections in the near field when full power is applied. Lowering the gain of the probe amplifier for near field visualization, conventionally referred to as range gain, does help but is not as effective as fixing the gain of the probe amplifier at the optimum signal-to-noise ratio and then continuously tailoring the transmit power to compensate for the predicted attenuation for a given depth. In accordance with the invention, at low tissue depths, low power is automatically provided. The system is designed to meet the standard of no more than 100 mW/cm$^2$ at its maximum power position. This is a standard set by the industry. Hence, the average power delivered to the human tissue is maintained below 100 mW/cm$^2$ under all conditions.

ELECTROSTATIC SHIELDING OF THE TRANSDUCER

In medical applications where life support instruments such as EKG, EMB, intravenous machines, etc. are connected to the patient, spurious electrical signals are quite often generated by the life support equipment and electrically coupled to the transducer when the transducer comes in contact with the patient. The transducer 100 of FIG. 10 in the present invention is electrostatically shielded to prevent the pickup of such electrical noise.

Figure 12:
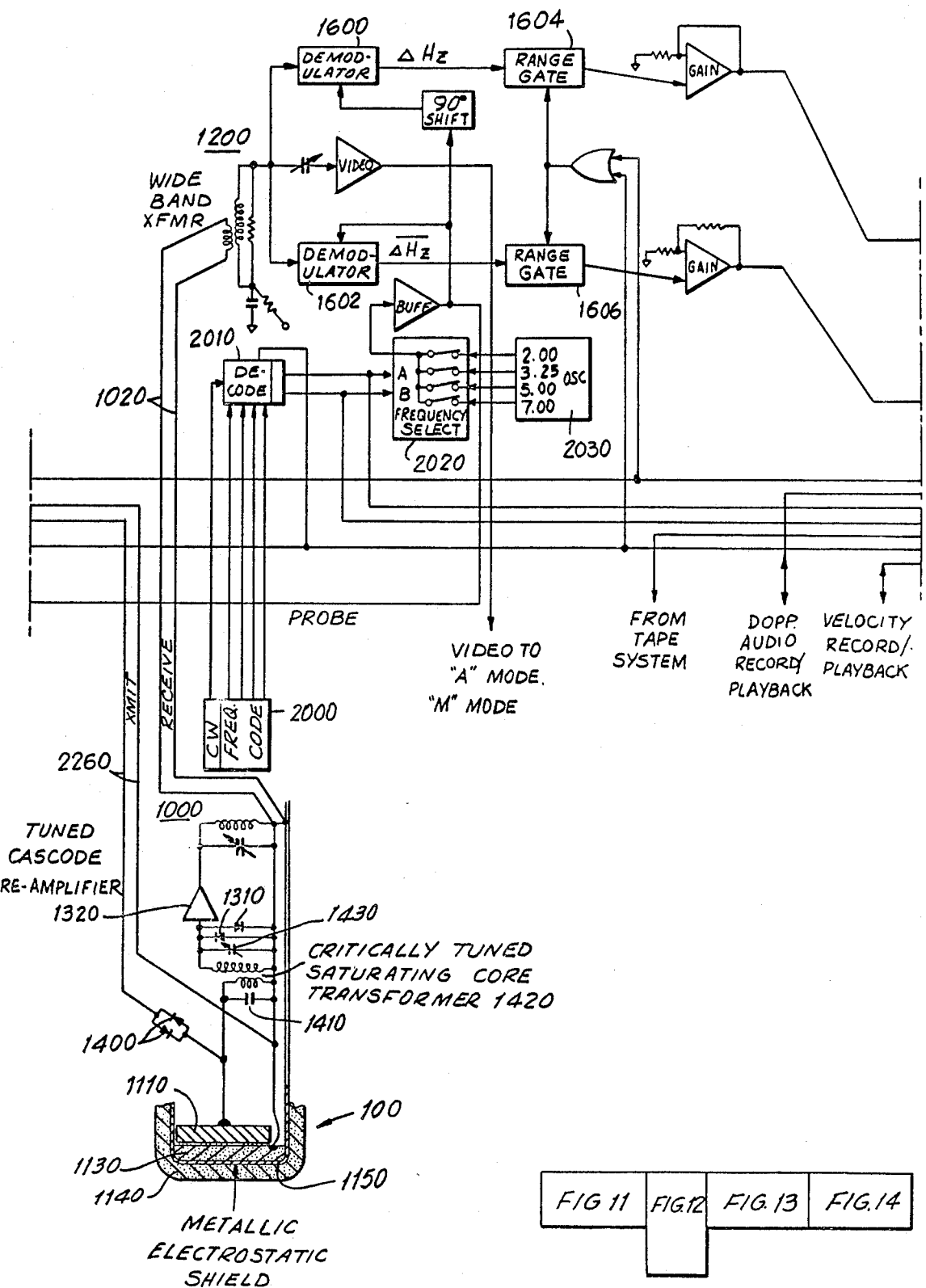
FIG. 12 illustrates the probe and demodulator circuits of the ultrasound diagnostic system in accordance with the invention.

As shown in FIG. 12, the transducer 100 is comprised of crystal 1110 conventionally interconnected to an output. In front of the crystal is conventionally placed epoxy layer 1130. A metallic layer 1150 is provided over the top of the epoxy 1130 and surrounding the edge of the crystal. A further epoxy layer 1140 is provided on the metallic layer. Of course, a variety of approaches can be utilized to provide electrostatic shielding to this probe tip. A wire screen could take the place of the layer 1150 or the like. It is important to note that electrical noise from the patient is intercepted by the electrostatic shield and is taken to the output of the amplifier rather than to the input so that the input signals to the amplifier are not subject to this noise. The need for the shielding is especially apparent when the signal-to-noise ratio of the probe electronics is increased to the level of this invention. In known devices having a significantly lower signal-to-noise ratio, sources of noise at this level are less apparent.

MINIMIZATION OF JOHNSON ELECTRICAL NOISE

Figure 15:
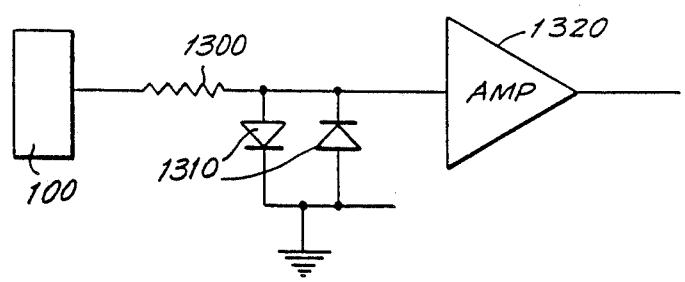
FIG. 15 illustrates a prior art interconnection between the ultrasound crystal and the receiver amplifiers.

As previously indicated, each narrow band amplifier 1000 is interconnected over cable 1020 to a wide band receiver 1200. One source of noise in ultrasonic systems, and in other systems where noise is a problem, is electrical noise caused by the electrical components of the system. One of the chief "noise" generators is the resistor in the conventional wide band receiver used in ultrasonic detectors. This is shown in FIG. 15 wherein the transducer 100 is connected through a voltage dropping resistor 1300 through a set of clamp diodes 1310 and into the amplifier 1320. The resistor 1300 is a primary electrical noise source in such conventional approaches.

The function of resistor 1300 in conventional designs is to prevent the amplifier protection diodes 1310 from shorting the transmit signal to ground during the transmit period. If the resistor 1300 is too small, a large portion of the transmit energy will be lost via resistor 1300 and amplifier protection diodes 1310 to ground. On the other hand, if the resistor 1300 is made too large, a portion of the receive signal will be lost according to the voltage divider effect of the resistor 1300 and the input impedance of amplifier 1320. A very significant source of noise is the Johnson noise of the resistor 1300 which increases as the resistance of resistor 1300 is increased. The present invention eliminates the use of this resistor. In the circuit shown in FIG. 12 the transducer 100 is connected through two diodes 1400 to the transmit circuit T. This is conventional. The transducer 100 is also connected in parallel across a capacitor 1410 and across the primary of a saturable core transformer 1420 to the receive circuit. The secondary of transformer 1420 is, in turn, connected in parallel to a variable capacitor 1430 which is in parallel across the pair of clamping diodes 1310 and to the input of amplifier 1320. As is apparent, the resistor 1300 of conventional circuits is eliminated.

During transmission of the Doppler pulse, the reactive components of capacitor 1410 and of the primary of saturable core transformer 1420 are tuned so that the voltage and current components are in phase (i.e., no reactive loss) and all energy from the transmitter is directly applied to the crystal 1110 and converted into ultrasonic energy. Of utmost importance is the construction of transformer 1420. The core material, placement of the primary and secondary windings, as well as the type of wire used is critical. Specifically, the transformer is designed to efficiently transfer the low level receive energy from the crystal to amplifier 1320 (i.e. with no greater than critical coupling). On the other hand, the coupling is such that the high level signal during the transmit period will detune the secondary and effect a minimal absorption of the transmit energy.

Hence, during the transmit phase, the receiver circuit is completely detuned from the transmit frequency. In the transmit phase, the only impedance in the circuit is the 50 ohms of the crystal 1110. During the receive time, any signal received by the crystal 1110 is converted into electrical energy and is delivered into the primary of transformer 1420 and is stepped up by a factor of 10. Again, because of the matching of the reactive components of capacitor 1430 and the secondary of transformer 1420, the reactive loss is substantially zero and the stepped up signal is delivered directly into the amplifier 1320. It is recognized that noise generated by components at the input Io amplifier 1320 is decreased by the square of the turns ratio of the transformer 1420.

Hence, the circuit of the present invention, as shown in FIG. 12, provides a signal-to-noise ratio five to ten times better than conventional approaches because it uses a narrow band circuit designed for a specific frequency (i.e., the frequency of one of the several probes) to have extremely low component noise. This is a significant increase in the signal-to-noise ratio of the design of ultrasonic systems. Hence, by utilizing a narrow band amplifier concept, as previously discussed, the Johnson noise directly attributable to the resistor 1300 in conventional circuits can be minimized by utilizing the transformer and capacitor circuit as shown in FIG. 12. The only significant noise left in the circuit of FIG. 12 is the crystal noise at room temperature. In comparison to wide band amplifiers of conventional band width, i.e. 5 MHz, the narrow band amplifier 1000 of the present invention has an approximate 1 MHz bandwidth. Furthermore, the circuit of FIG. 12 is readily adaptable at the factory to the frequencies of each of the several probes.

As shown in FIG. 12, the second stage of amplification which is remote from the hand-held probe is a wide band receiver capable of receiving the several separate probes of the present invention. The wide band receiver 1200 is designed to receive 1–10 MHz and will accommodate any one of the several probes. An impedance matching circuit as shown in FIG. 15 is utilized to connect each of the probes to the wide band receiver 1200.

CONTINUOUSLY TRACKING PRF FILTERS

As mentioned above, the pulse repetition frequency (PRF) is varied by retransmitting the Doppler pulse bursts at a fixed time, T, after the cessation of the range gate. Since there is only one sample of the signal taken in each Doppler transmit frame, the range-gated sample frequency is the same as the PRF. According to the sample theorem, the maximum detectable Doppler shifted frequency is slightly less than one half the sample frequency. Therefore, the high frequency roll-off characteristics of the low pass PRF filter 1608 has a 3 db point at one half the PRF with a steep roll-off of 72 db/octave, i.e., 72 db attenuation at the PRF. Of course, this filter, according to the invention, tracks the PRF continuously. As discussed with reference to FIG. 12, the received signals are applied to dual demodulators 1600 such as product detectors and 1602. Here the received signal is compared with the transmitted oscillator frequency in 1600 and the transmitted frequency shifted 90 degrees in phase in demodulator 1602.

Figure 13:
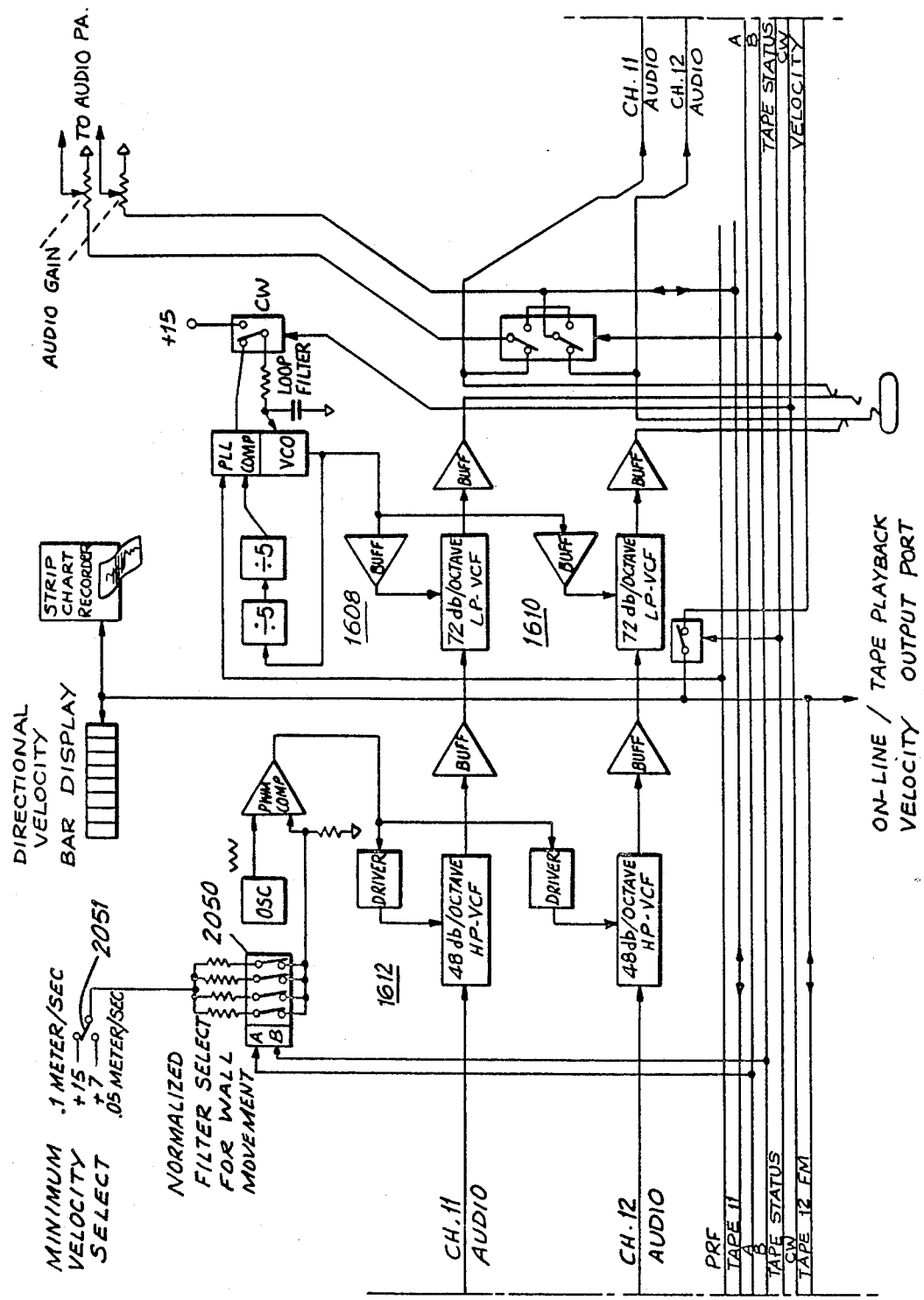
FIG. 13 illustrates the filter circuits of the ultrasound diagnostic system in accordance with the invention.

This demodulator feature is known and produces two signals, one leading and one lagging (this is commonly referred to as quadrature audio signals). For example, if a signal from demodulator 1600 leads, then the blood is flowing in one direction whereas if it lags the signal from demodulator 1602, then the blood is flowing in the other direction. The demodulated signal is applied to a range gate circuit 1604, 1606 which, as previously discussed, allows the system to analyze the reflected signals only in a predetermined range of time. The reflected Doppler shift frequencies are then applied to dual voltage tunable PRF filters 1608 and 1610 (FIG. 13). These dual low pass filters have tunable high frequency cut-off characteristics which remove the high frequency PRF signals. As discussed, the PRF frequency is higher at shallow depths and lower at greater depths. Therefore, the tunable filters decrease their cut-off frequencies at greater depths. Previous systems utilized a number of fixed PRFs and matching filters. Using this method, the optimal PRF is seldom achieved for a given depth. In addition, a selectable low frequency cut-off filter is provided to remove low frequencies, including possible beat frequencies seen in FIG. 13, the cutoff of the high pass filters 1612 frequency may be selected by the operator, with the switch 2051, in terms of blood velocity rather than cycles, the setting being normalized to all probe frequencies by filter select 2050. These filters remove the Doppler pulse repetition rate frequency and slow-moving wall frequencies from the audio signals while preserving all frequencies which carry valid velocity information. Hence, referring to FIG. 13, as the tracking circuit which is controlled by the control 600 of FIG. 11 is set for greater and greater depth, not only is the power to the transmitter increased but also the PRF cut-off frequency is decreased.

PEAK SWITCHING FULL WAVE QUADRATURE AUDIO DEMODULATOR

The signals are then delivered into an audio demodulator 1705. The audio demodulator 1705 (FIG. 14) processes the signals from the tunable PRF filters 1608 and 1610 into a clean signal for display purposes. The quadrature audio demodulator of the present invention has the following characteristics:

1. Works well with signal-to-noise ratios as low as 1.5 to 1.

2. Has a wide dynamic range (1000 to 1)—signal levels from 10 mV peak-to-peak to 10 V peak to peak.
3. Completely ignores the riding high syndrome.
4. Maintains phase relationships of the quadrature signals, for accurate flow direction determination.
5. Provides a threshold adjustment to eliminate background noise.
6. Operates over a frequency bandwidth from 10 Hz to 20 kHz with no significant phase shift over this entire frequency band.
7. Low cost; uses only six low-cost integrated circuits.
8. Uses full wave demodulation for fast responses and accuracy.
9. Provides a fast rise time (15 ms to 90% rise time).
10. The output voltage follows the mean of the velocity distribution.

Figure 14:
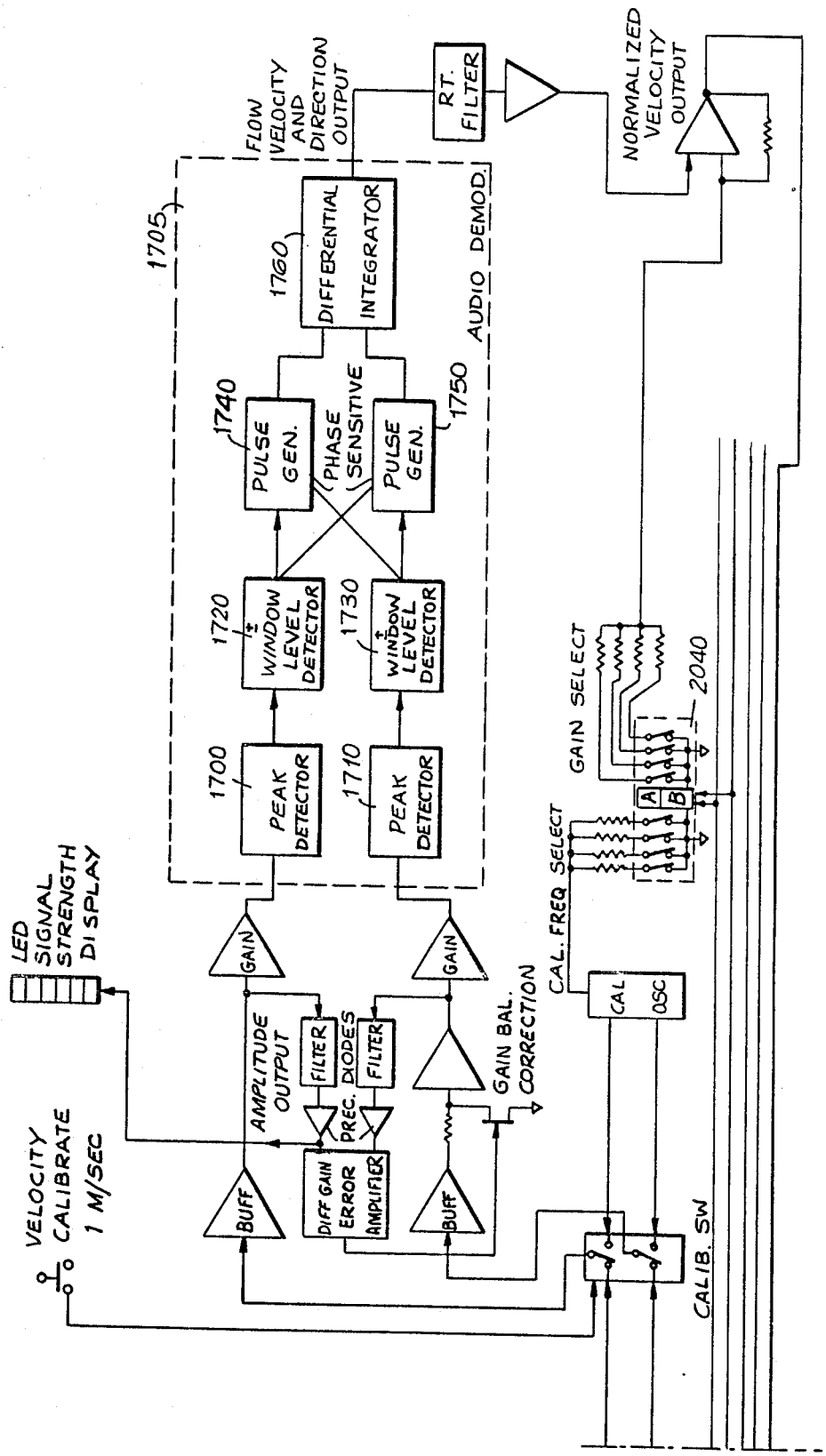
FIG. 14 illustrates the demodulation circuits of an ultrasound diagnostic system in accordance with the invention.
Figure 16A:
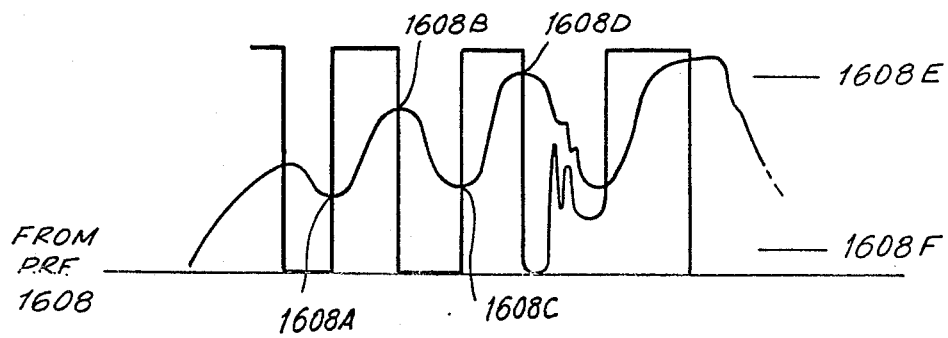
FIG. 16a illustrates the output of one peak detector.
Figure 16B:
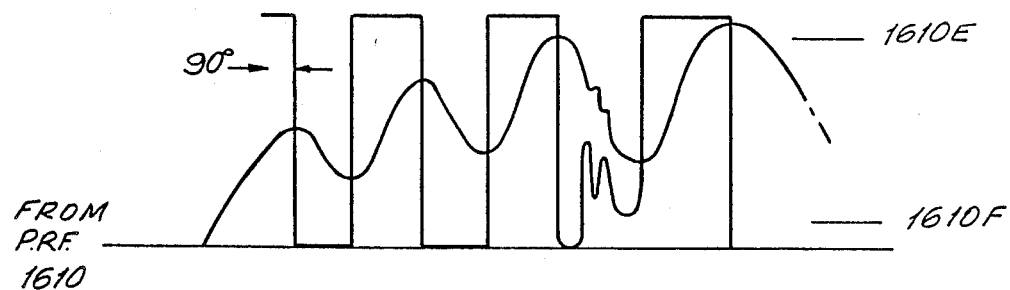
FIG. 16b illustrates the output of the other peak detector.

This feature of the invention is best described by reference to FIG. 14. Signals from the PRF filters 1608 and 1610 are delivered into dual peak detectors 1700 and 1710. These peak detectors receive signals as shown in FIG. 16 from the PRF filter 1608 and 1610. The two signals are identical except they are separated by 90 degrees in phase. The Doppler signal which is represented by the sinusoidal curve may be riding on another curve such as a DC level or other level. The purpose of the peak detectors 1700 and 1710 is to eliminate the effects of these other levels including low frequency noise and base line voltage shifts.

Hence the need exists for the detection of the maxima and the minima of the Doppler-shifted audio signals shown in FIG. 16, rather than the detection by a conventional zero crossing detector. The peak detectors 1700 and 1710, through a unique gain switching technique, provide a constant level output signal which reverses precisely at peak turn-arounds, shown as 1608A, B, and C. However, note the perturbations denoted by 1608D. The output signal has gain but it is insufficient to reach the levels 1608E or 1608F. Herein lies the key to the operation of the demodulator circuitry. The circuit components can be adjusted to reject small excursions such as 1608D, thus providing a means of rejecting instrument background noise, while meeting the specifications listed above.

Since the peak detectors determine most of the desirable characteristics of the quadrature audio demodulator, they will now be discussed in greater detail. The peak detection circuit is obtained from the conventional operational amplifier circuit of FIG. 17B by the addition of a non-linear feedback element, as shown in FIG. 17C and as will be described hereinafter.

Figure 17:
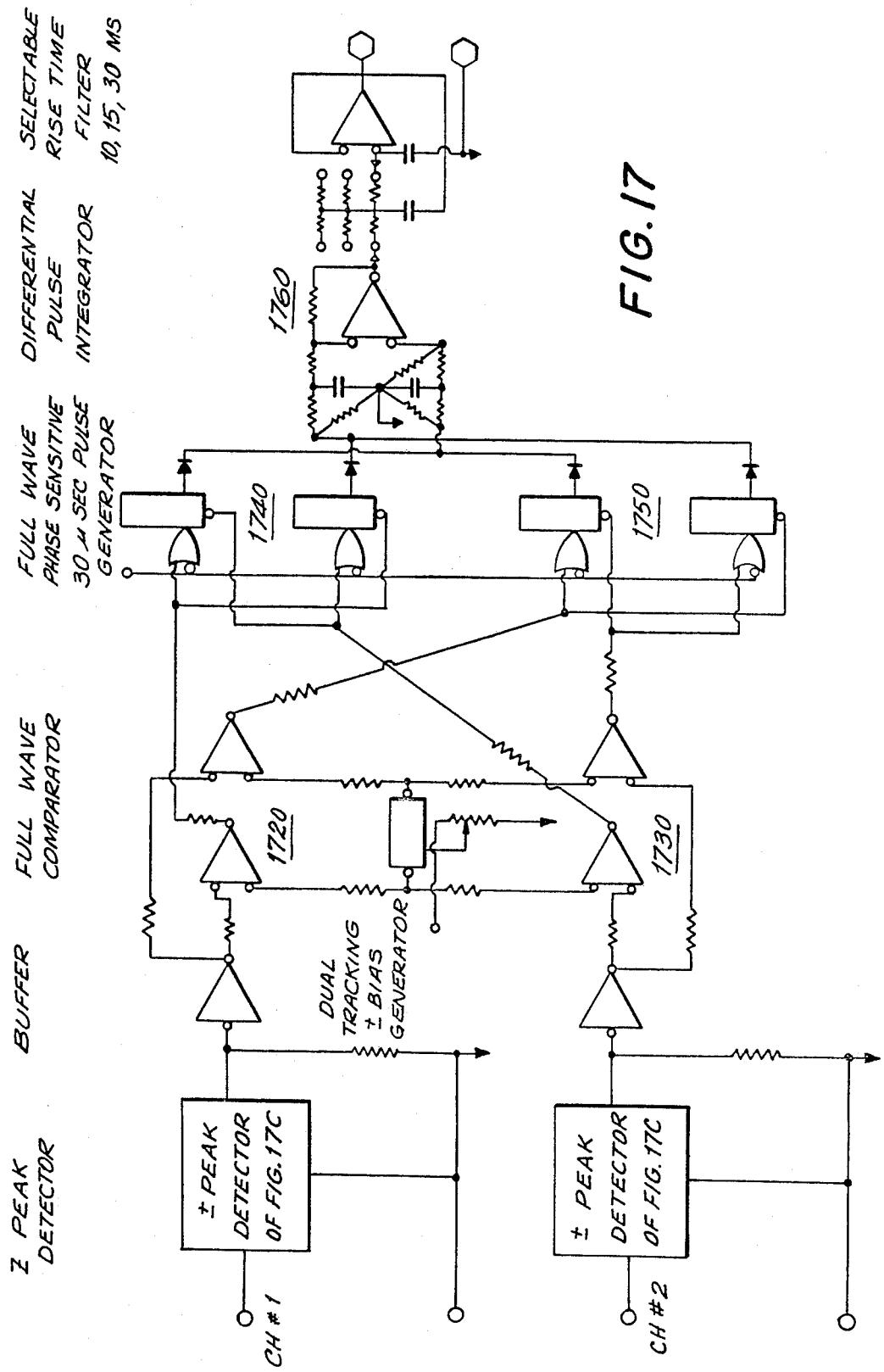
FIG. 17 is a simplified diagram of a preferred embodiment of the quadrature amplifier/demodulator in accordance with the invention.
Figure 17A:
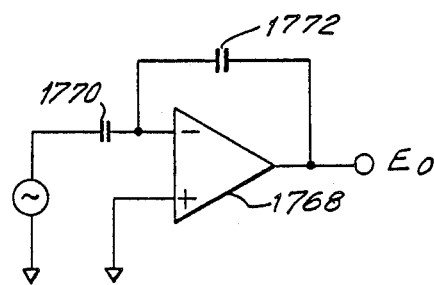
FIG. 17a illustrates an operational amplifier circuit.
Figure 17B:
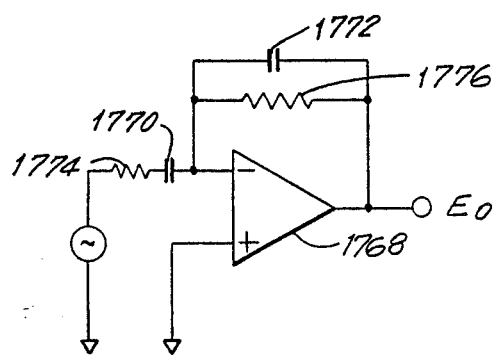

Operation of the circuit of FIG. 17B, as it is employed for this purpose, is more readily understood with reference to the simpler circuit of FIG. 17A. If the amplifier 1768 of FIG. 17A is chosen to have characteristics similar to the LF357 integrated circuit operational amplifier, the circuit of FIG. 17A will have a gain of C1/C2, where C1 and C2 are the capacitances of capacitors 1770 and 1772 respectively, over the frequency band of interest, i.e., from 20 Hz to more than 20,000 Hz, provided the capacitances are small. For example if C1=3000 pf and C2=10 pf, the circuit of FIG. 17A will have a gain of 300 and there will be no significant phase shift since the circuit resistance values are large, i.e., the input impedance of the amplifier 1768 is $10^{12}\Omega$.

If we add to the circuit of FIG. 17A resistors 1774 and 1776 having resistances R1 and R2 respectively, shown in FIG. 17B, where R1 is small, for example, R1=50$\Omega$, and R2 is very large, for example, R2=$2\times10^9\Omega$, the performance is improved by the damping properties of resistor 1774 and the ability of resistor 1776 to minimize the zero drift when no signal is present. The values of R1 and R2 are such that the changes in the gain and phase shift characteristics from those of FIG. 17A are not significant.

Figure 17C:
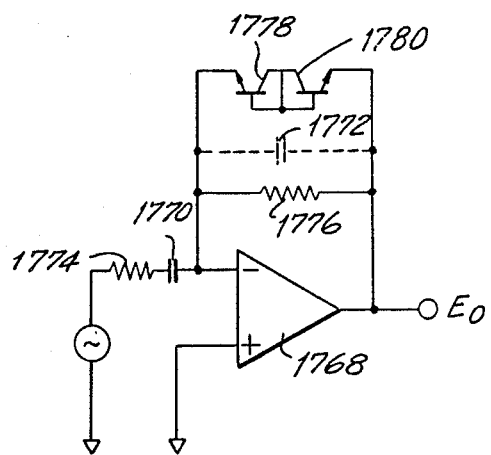
FIG. 17c illustrates a peak detector derived from the circuit of FIG. 17b.

In the peak detection circuit shown in FIG. 17C, transistors 1778 and 1780 have been added. Transistors 1778 and 1780 are connected as back-to-back zeners that are selected for the following characteristics: (1) low capacitance, (2) extremely sharp break point, and (3) fast response. Transistors such as the 2N2222 function well in this mode. When the reverse-biased zener of the transistor pair 1778, 1780 is not conducting, the circuit acts the same as the circuit of FIG. 17B, having a gain on the order of 300. However, when the zeners are conducting, the impedance of the feedback element approaches zero; and the circuit acts as a unity gain voltage follower. Note that when the zeners are conducting, the operational amplifier operates in such a way that the input node P is held at a potential which differs from the output voltage $E_o$ by a fixed amount approximately equal to the zener voltage. As the magnitude of the output $E_o$ increases, conduction through the zeners raises the voltage at P so that this difference remains constant. Hence, any time the magnitude of $E_o$ begins to decrease, the voltage difference between the output and node P drops below the zener voltage, the zeners stop conducting and the gain of the circuit goes to its high value (e.g., 300).

If the circuit component values are chosen for a gain of 300 and the input signal is such that the zeners (1778 and 1780) are in the conducting state, instantaneously upon the reversal of direction of the input signal, the amplifier gain will change to 300, and the output voltage will reverse polarity and track the input signal with a gain of 300. This condition will continue until the zener level is reached and once again the amplifier gain will revert back to unity. The amplifier will remain in this unity gain state until the input signal once again reaches a maximum or minimum and changes direction. On the other hand, if the changes of the input signal are not large enough to reach the zener levels, the output signal will simply track the input signal with a gain of 300.

It is also noted that capacitor 1772 is now drawn in dashed lines since the distributed capacitance of the feedback elements may very easily add up to 10 pf and the capacitance C1 can be adjusted to give the desired circuit gain.

The pulses are then delivered to the window level detectors 1720 and 1730, which eliminate the noise perturbations such as 1608D by extending pulses only having levels extending beyond 1608E and 1608F. These pulses are then applied to phase-sensitive, full-wave pulse generators 1740 and 1750 comprised of pairs of one-shots, as shown in FIG. 17. Either of the generators 1750 or 1740, but not both, will generate pulses of equal amplitude and width depending on the phase of the signals at that instant. Thus, the pulses of the leading channel enable the pulse generator of the lagging channel. This condition reverses as flow direction reverses. These pulses are then integrated by the differential integrator 1760 to provide blood flow velocity and direction information.

For a given velocity of blood flow the Doppler frequency will increase as transmit frequency is increased. This has been a confusing issue in past instruments since velocity is given in cycles rather than meters/sec. The signal output of this instrument is normalized to meters/sec regardless of transmit frequency and an internal calibrator is provided for operator convenience.

The present invention can now present the above signals for accurate but simple analysis of cardiac output, velocity and volume blood flow to the brain, heart valve timing measurements, etc.

THE OPERATION OF THE SYSTEM

As illustrated in FIG. 12, the probe includes a frequency coder 2000 and mode selection continuous wave vs. pulsed Doppler, which may comprise a terminal block having determined shorts. This coder is connected to a decoder 2010 in the demodulation circuit, for controlling automatically a frequency selector 2020 (for example, an electronic gate) to select the corresponding oscillator frequency of oscillator 2030. This selection is also effective automatically for the other frequency-dependent parameters such as the gain select 2040 of FIG. 14 and the normalized filter selection 2050 of FIG. 13.

The oscillator output is applied to the comparator 2060 of FIG. 11, serving to convert the sine wave oscillator output to inverted and noninverted output. The non-inverted output is applied to a divide-by-eight divider 2070, for synchronization of the start time of a range depth one-shot 2080, the width of the output of the one-shot 2080 being determined by the control 600 which may be a potentiometer. The output of the range depth one-shot is applied to the enable input of a range gate width one-shot 2090 for controlling the gate width by means of a potentiometer 2100. The clock input of the range gate width one-shot is derived from an anti-jitter circuit 2110, to which a divide-by-four output of divider 2070 is applied. The anti-jitter circuit, which will be described in later paragraphs, insures that the start of the range gate does not shift relative to the transmit pulse, since shifts even in the nanosecond range can produce undesirable outputs, i.e., noise that may be larger than the Doppler signal. The non-inverted range gate width output is applied to a range sample one-shot 2120, and thence to a range sample and hold circuit 2130, for providing an output to a liquid crystal display 2140 for continuously displaying the range gate timing, and hence the depth of the sample volume.

Retransmit one-shot 2150 determines the time for retransmission of the pulse Doppler burst following termination of the range gate, in order to insure maximum sampling rates, and one-shot 2160 determines the minimum delay between successive Doppler pulses. The retransmit one-shot is controlled by way of the anti-jitter pulse shaper 2170 and flip-flop 2180, to insure that no jitter occurs in the timing of the pulse.

The transmit gate control is started by gate start one-shot 2190, and stopped by the gate stop one-shot 2200, these circuits controlling the gate width circuit 2210 which is comprised of a plurality of flip-flops, e.g., four flip-flops. This circuit controls the number of cycles in each pulse burst, and may be controlled by an external switch 2220. The output of the transmit gate width flip-flops and the oscillator frequency signals are applied to the transmitter amplifier 2230 by way of NAND gates 2240, 2250, thus controlling the number of cycles of transmission of the pulse Doppler bursts on lines 2260 to the probe.

The range gate is outputted from the circuit of FIG. 11 on line 2270, to provide control of tunable filters and gating signals in the receiver at precise intervals.

When echo pulses are also transmitted, in accordance with the invention, the echo frame is determined by one-shot 2280, and the echo frequency is determined by one-shot 2290. This circuit further includes a pre-echo minimum one-shot 2300, a one-cycle delay one-shot 2310 and a half-cycle delay one-shot 2320, various one-shots of this circuit being connected to the NAND gates 2240, 2250 in order to insure the blocking of the Doppler pulses during the echo period. The output of charge echo capacitor one-shot 2330 is applied to the transmitter output transformer 2360 by way of transformer 2340 and power MOSFET power amplifier 2350 to charge capacitor 2335.

In the pulse Doppler mode the transmit power is controlled automatically with reference to an operator-selected maximum power level by a control 2400. This control allows the operator to select a power range suited to individual patient variability, for example, an infant versus an older obese patient. The transmit power is then controlled automatically according to the range gate time and pulse duration as presented subsequently.

Transmit energy levels during Doppler transmission are determined by monitoring the mean current supplied by the transmit power stage 2230, i.e., a voltage is developed at 2235 proportional to the mean current supplied by the transmit power amplifier 2230. This level is compared to a preset reference level as set by control 2410 at the power error amplifier 2420 which effects a correct voltage level to the power output stage. In this manner the average current level of the transmit power amplifier is held constant and the power delivered to the transducer is continuously and automatically adjusted as the transmit duty cycle is changed, for example, by changing the PRF, the number of cycles transmitted or the frequency of transmission. The desired power requirement vs. depth and transmit frequency is thus achieved automatically.

It is important to note that the transmit voltage requirements may be quite different for the echo frame vs. Doppler frames, i.e., the Doppler may be operating at a high PRF in the near field and echo frame may be receiving signals from 17 cm. These requirements are met in the following manner: after the last Doppler frame and prior to the echo frame, capacitor 2335 is charged to 100 volts by echo power circuitry. Thus, the energy for the single-cycle, pulse for the echo frame is supplied by capacitor 2335. Diodes 2450 ensure that there is no interaction between the pulse Doppler power requirements and the echo amplitude.

The continuous wave line illustrated in this figure enables transmission of continuous radiofrequency signals to the crystal by enabling operation of switch 2265, which applies the oscillator output directly to the probe, in response to the insertion of a continuous wave probe (not shown).

Figure 19:
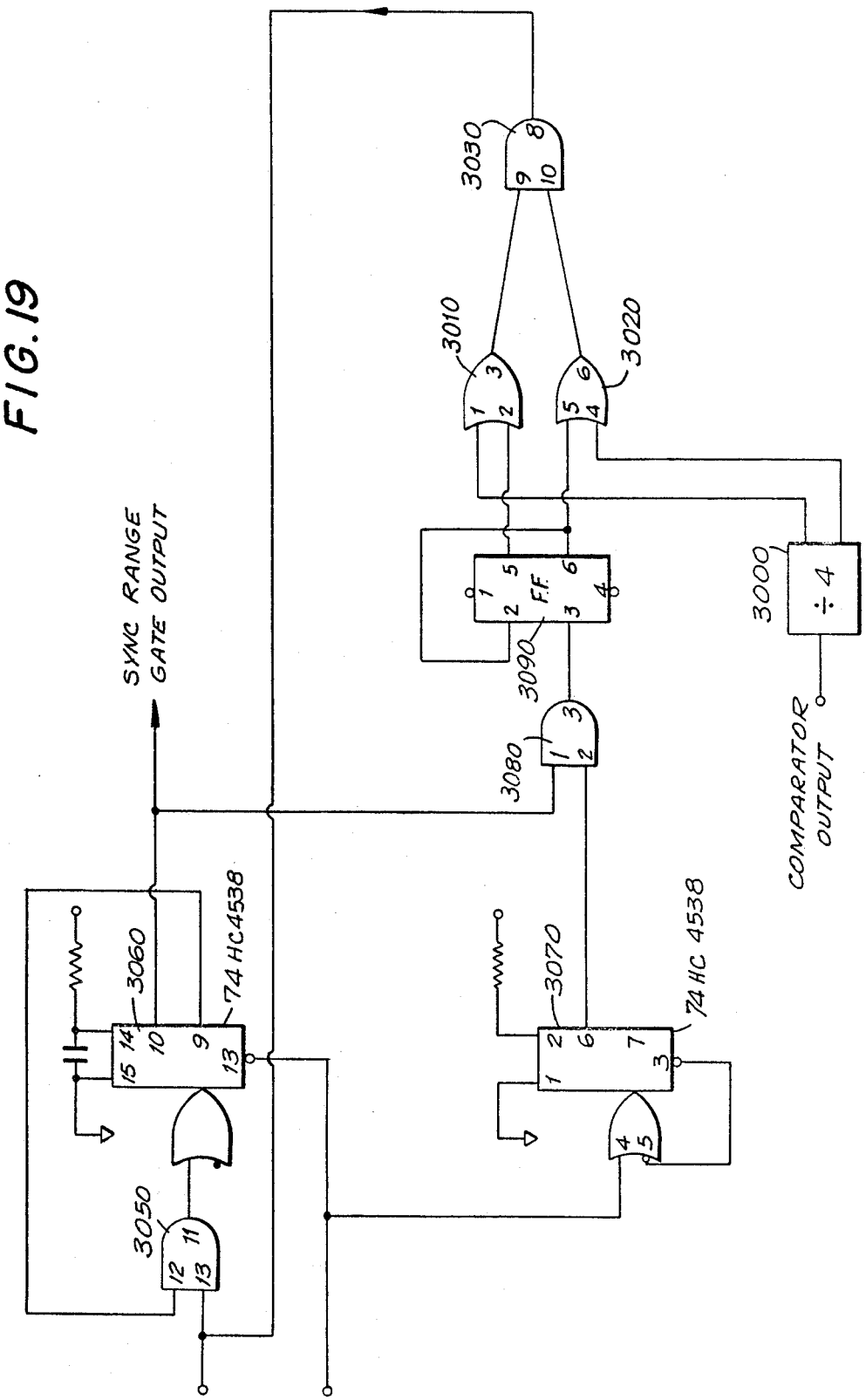
FIG. 19 is a block diagram of an anti-jitter circuit.

Referring now to FIG. 19, therein is shown one embodiment of an anti-jitter circuit in combination with the range gate synchronization circuitry. In this circuit, inverted and non-inverted outputs are provided from a divide-by-four circuit 3000 whose input is coupled to an output of the comparator 2060, the output of the divide-by-four circuit being selected via OR gates 3010, 3020, for application to AND gate 3030. The output of the AND gate 3030 clocks the range gate one-shot 3060 via AND gate 3050.

The output of the one-shot 3060 at terminal 10 is the synchronized range gate output. One-shot 3070 is clocked via the enable input of the one-shot 3060, and its output at terminal 6 is ANDed with the synchronized range gate output via AND gate 3080, to control flip-flop 3090. The inverted and noninverted outputs of flip-flop 3090 are applied as the second input of the OR gates 3010, 3020.

The time $T_w$ must, in accordance with the invention, be held exactly constant, since it has been found that noise within the frequency range of the Doppler signal will be generated if the start of the range gate intercepts a slope of the echo signal (as would be seen if the range gate coincided with a signal from a reflecting boundary) at different times, even with different timings on the order of nanoseconds.

In this system we use the divided transmit frequency as a clock. The start of the range gate is synchronized in time with the start of the transmit pulse and therefore cannot deviate from this timing. In order to ensure that the timing is positively selected, i.e. does not flip back and forth between clock pulses, the anti-jitter circuitry, comprised of one-shot 3070, AND gate 3080 and flip-flop 3090, selects the phase of the clock pulse that will not allow coincidence between the clock pulse and the enable pulse.

PROBE SWIVEL MECHANISM

In a probe having an electrical transducer at its tip, such as an ultrasound transducer probe used in medical diagnosis, it is sometimes desirable to change the orientation of the transducer relative to the probe handle. The mechanism by which the orientation of the transducer is changed must not twist or stretch the wiring to the transducer. Further, the mechanism should normally be compact, so as not to add excessive bulk to the probe and the wiring from the transducer to the probe handle should be protected from mechanical damage.

The swivel mechanism disclosed herein meets these criteria.

Figure 20:
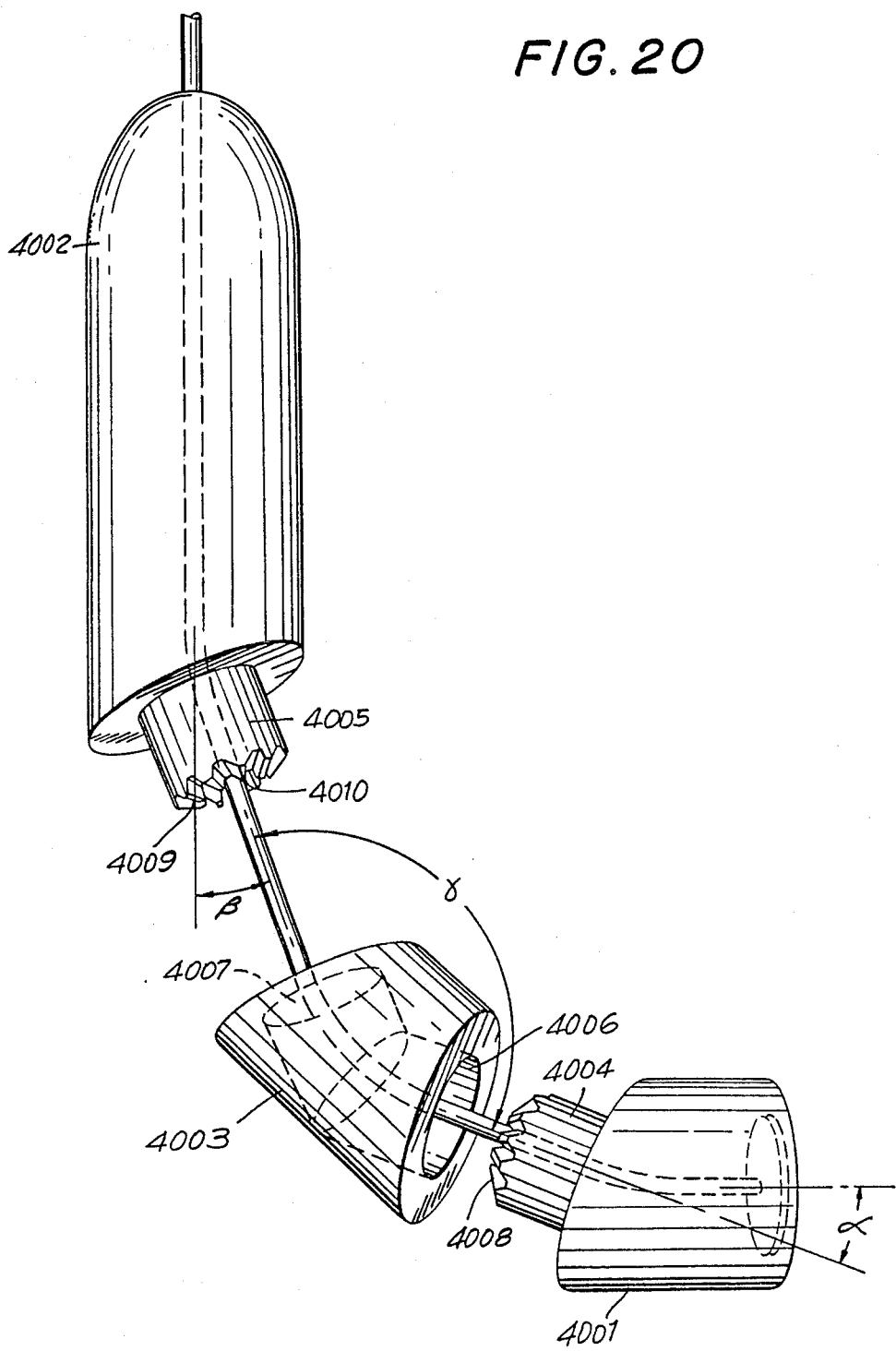
FIG. 20 is an exploded view of a swivel probe.

The swivel mechanism consists of three major parts, as shown in FIG. 20: the nose portion 4001 (which normally houses the transducer), the probe handle 4002, and the adjusting sleeve 4003. Cylindrical projections 4004 and 4005 extend from the nose portion 4001 and from the handle 4002. These insert into mating bores 4006 and 4007 in the adjusting sleeve 4003 and are held into these bores by retaining means (not shown) which permit the projections to rotate relative to the adjusting sleeve. The ends of the cylindrical projections 4004 and 4005 comprise bevel gears 4008 and 4009. These gears are maintained in proper mesh by the adjusting sleeve 4003 and its retaining means.

The angle between the probe 4002 and the nose portion 4001 is adjusted by turning the sleeve 4003 relative to the handle 4002.

The angular orientations of the projections 4004 and 4005 and bores 4006 and 4007 determine the range of adjustment of the mechanism. If $\alpha$ is the angle between the axis of the nose portion 4001 and the axis of its projection 4004; $\beta$ is the angle between the axis of the handle 4002 and the axis of its projection 4005; and $\gamma$ is the angle between the axes of bores 4006 and 4007, then the maximum range of adjustment is from $([\alpha-(180°-\gamma/2)]+[\beta-(180°-\gamma/2)])$ to $([\alpha+(180°-\gamma/2)]+[\beta+(180°-\gamma/2)])$. For the simple, symmetrical case where $\alpha=\beta$ and $\alpha+\beta+\gamma=180°$, this range is from 0 to $4\gamma$. Hence, to obtain an adjustment from 0° to 90°, $\alpha$ and $\beta$ are 22.5°, and $\gamma$ is 135°.

In order for such a swivel to provide co-axial alignment of the handle 4002 and the nose portion 4001 at one extreme of the range of adjustment, the bevel gears 4008 and 4009 must differ in alignment by $\frac{1}{2}$ gear pitch relative to the plane defined by the axis of the part and the axis of its cylindrical projection.

As a matter of preferred design, each of the bores 4006 and 4007 and each of the projections 4004 and 4005 commences from a plane surface perpendicular to its axis. This permits full surface contact between the ends of the adjusting sleeve 4003 and their mating surfaces on the probe handle 4002 and nose portion 4001.

Wiring between the transducer and the probe handle is routed through bores central to the projections 4004 and 4005, for example, bore 4010, and generally through the intersection of bores 4006 and 4007. Since this route corresponds approximately to a line of constant length, the wiring experiences essentially no stretching or compression as the nose portion orientation is adjusted.

Since mesh between the gears 4008 and 4009 prevents relative rotation between the projections 4004 and 4005, the wiring experiences no twist as the orientation of the nose portion is adjusted.

The wiring through the mechanism is protected from mechanical damage by the sleeve 4003.

The present invention is thus characterized by the following features:

1. Interlaced "Doppler" and "Echo" Transmitted Pulses Provision of single-cycle ultrasound pulses to provide echo visualization beyond the Doppler range gate setting which are interlaced with a train of Doppler pulses used for velocity measurements as shown in FIG. 6. The time interval between echo pulses remains constant and independent of Doppler pulse repetition rate (PRF) as does the power of each echo pulse.
2. Transmit Receive Capability—enables the following modes:
   A. Using the pulsed Doppler probe:
      1. Pulsed Doppler only.
      2. Pulsed Doppler interlaced with echo.
   B. Using the continuous wave probe:
      1. Continuous wave only.
      2. Pulsed Doppler only.
      3. Pulsed Doppler interlaced with echo.
   3. Range Tracking Transmit Power for Doppler Pulses—The transmitted power of the ultrasound pulses for Doppler measurements automatically tracks the range gate depth setting so that the greater the depth, the greater the power. The power at a particular depth setting is chosen so that the aggregate signal-to-noise ratio for the tissue-receiver combination is nearly maximized for all range gate depths.
4. Range Tracking Pulse Repetition Rate for Doppler Pulses—A reciprocal relationship is automatically maintained between the Doppler pulse repetition rate and the range gate depth setting. In other words, as the range gate depth is set for greater depths, the Doppler pulse repetition rate is lowered and for shallower depths, the pulse repetition is increased. The Doppler pulses are transmitted a set time after the range gate setting. For any range depth, therefore, this arrangement maximizes the effected data sampling rate and determines the maximum flow velocity which can be measured.

5. Synchronized Range Gate—eliminates noise generated by unsynchronized range gate sample times characteristic of other pulse Doppler systems.

6. PRF Tracking Filters—The provision of the dual low-pass filters 1608 and 1610, to provide a tunable high frequency cut-off which decreases the cut-off frequency as the range gate depth increases. These filters remove the Doppler repetition rate frequency from the quadrature audio signals while preserving all frequencies which carry valid velocity information for all pulse repetition rates.

7. Dual tunable high pass filters 1612 normalized to low velocity roll off, i.e. 0.05 or 0.1 meters per second, eliminate velocities of no interest such as vessel wall motion, artifacts due to breathing, etc.

8. A Plurality of Narrow Band Probe Amplifiers for Received Signals—The provision of a plurality of tuned narrow band amplifiers each of which is actually located in its individual probe and which provides all signal gain needed for input to a wide band amplifier. The narrow band amplifier has its input impedance critically tuned to the crystal to minimize Johnson noise and to provide maximal obtainable signal-to-noise ratio at a specific frequency. The output impedance of this amplifier is matched to the combination of a probe cable impedance and wide band amplifier input impedance. This amplifier design substantially improves the signal-to-noise ratio of the return signal.

9. The velocity output signal is normalized to meters per second.

10. Full Wave Quadature Audio Demodulator—The audio demodulator of the invention detects the timing of the relative voltage maxima and minima as an economical means of obtaining a mean velocity signal. The demodulator preserves the phase relationship (direction information) and the magnitude of the velocity. Unlike conventional zero-crossover detectors, the circuit of the invention is insensitive to baseline voltage shifts and low frequency noise. Therefore, it can provide an accurate flow signal even in difficult clinical situations where the Doppler signal-to-noise ratio may be as much or tenfold below the useful ratio for zero-crosses.

11. Wide Band Amplifier—The use of a wide band amplifier, as shown in FIG. 12, permitting one system to be used with several different critically tuned probes at different frequencies typically in the range of 1-7 MHz.

12. Electrostatic Shielded Transducer—As shown in FIG. 12, the transducer of the present invention is electrostatically shielded and grounded to a separate electrical ground.

13. Swivel Probe—As shown in FIG. 10, a swivel probe is provided. The center of the swivel is hollow to permit the passage of electrical wires. The probe may be swiveled continuously throughout its range of adjustment without disrupting the electrical connection.

14. Signal Recorder—The invention also incorporates a recorder which can record Doppler flow information along with simultaneously measured physiological variables.

Figure 18:
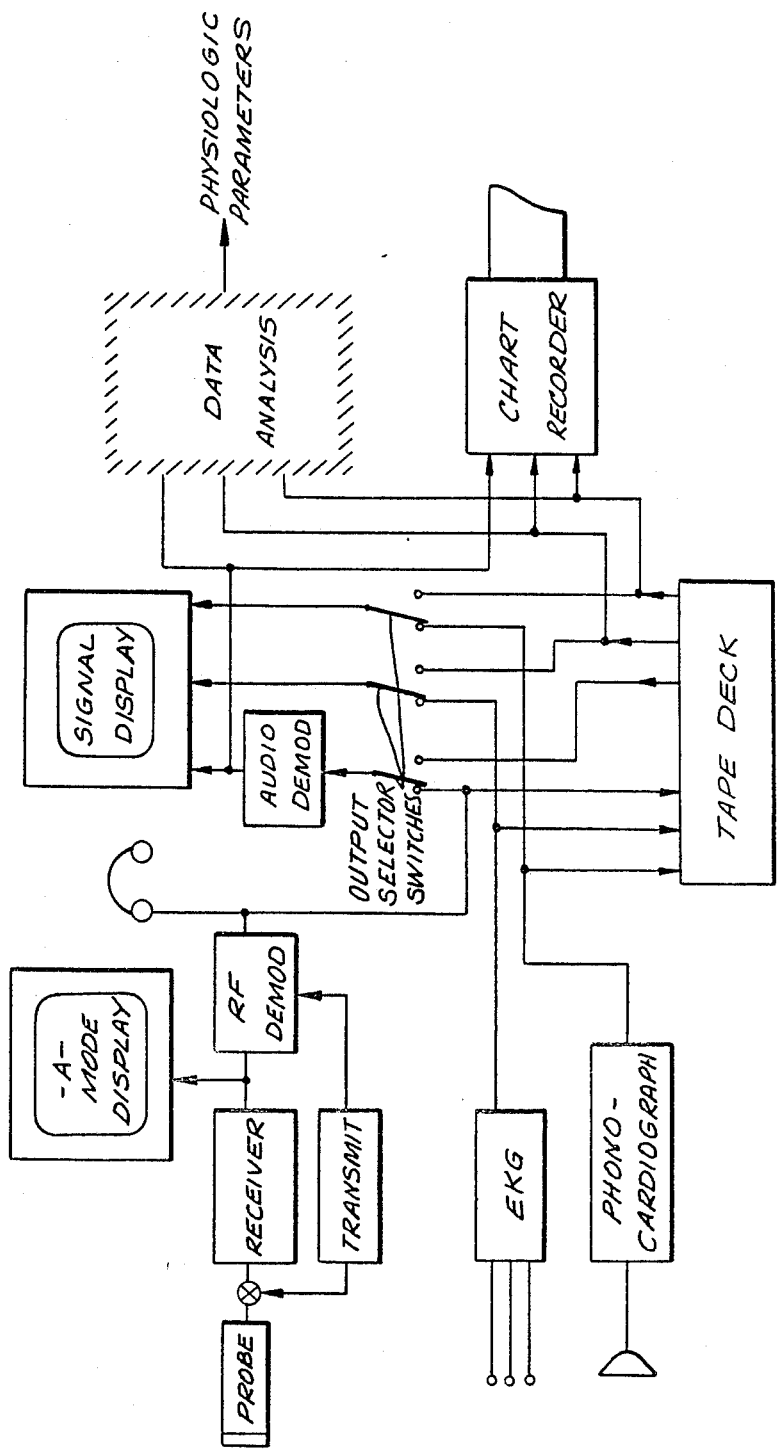
FIG. 18 is a block diagram of the system of the invention interconnected with suitable displays, recording devices, etc. for use.

The quadrature audio demodulator is illustrated in greater detail in FIG. 17. In this system it is noted that the plus-minus peak detectors are shown for the noninverting mode, but they may be used in the inverting mode. The latter mode is preferable. The system of the invention, incorporating various displays, and outputs and inputs, is illustrated in FIG. 18.

It is of course apparent that some of the above features have application to areas of discipline other than that of the Doppler ultrasound technology, and it is hence intended that this invention encompasses such additional application.

What is claimed is:

1. In an ultrasonic diagnostic apparatus including a transmitting means for generating drive signals, a receiving means for producing output signals for diagnosis, and ultrasound transducer means connected to said transmitting means for emitting ultrasound pulses in response to said drive signals and for apply signals to said receiving means in response to ultrasound pulses received in response to said emitted ultrasound pulses, the improvement wherein said transmitting means comprises means for generating a train of Doppler pulse signals each comprised of a burst of a plurality of cycles followed by a receiving cycle, means for generating range gate signal for applying gate signals to said receiving means to enable reception of signals, by said receiving means corresponding to said Doppler pulse signals only during predetermined periods following each Doppler pulse signal, means for applying said Doppler signals to said transducer means as said drive signals, and means for adjusting the time between each Doppler pulse signal and the respective range gate signal while maintaining the time between each Doppler pulse signal and the immediately preceding range gate signal substantially constant and while simultaneously varying the power of emitted ultrasound pulses in the same sense.

2. The ultrasonic diagnostic apparatus of claim 1, wherein said means for generating a range gate signal comprises means for establishing first and second clock signals of opposite phase, and means responsive to substantial coincidence between the leading edge of said range gate signal and one of said first and second clock signals for initiating said range gate signal with the other of said click signals, said one clock signal being that one of said clock signals that initiated the last previous range gate signal.

3. In an ultrasonic diagnostic apparatus including a transmitting means for generating drive signals, a receiving means for producing output signals for diagnosis, and ultrasound transducer means connected to said transmitting means for emitting ultrasound pulses in response to said drive signals and for applying signals to said receiving means in response to ultrasound pulses received in response to said emitted pulses, the improvement wherein said transmitting means comprises means for generating a train of Doppler pulse signals each comprised of a burst of a plurality of cycles followed by a reading cycle, means for generating a range gate signal for applying gate signals to said receiving means to enable reception of signals only during predetermined periods following the emission of each Doppler pulse signal, means for applying said Doppler pulse signals to aid transducer means, sand means for adjusting the time between each Doppler pulse signal and the respective range gate signal and maintaining the time between each Doppler pulse signal and the immediately preceding range gate signal substantially constant while simultaneously varying the pulse repetition rate of said Doppler pulse signals.

4. The ultrasound diagnostic apparatus of claim 3 wherein said means for adjusting comprises means for inhibiting the generation of each Doppler pulse signal until a predetermined minimum delay time following the range gate signal corresponding to the previous Doppler pulse signal.

5. In an ultrasonic diagnostic apparatus including a transmitting means for generating drive signals, a receiving means for producing output signals for diagnosis, and ultrasound transducer means connected to said transmitting means for emitting ultrasound pulses in response to said drive signals and for applying signals to said receiving means in response to ultrasound pulses in response to the emitted ultrasound pulses, the improvement wherein said transmitting means comprises means for generating a train of Doppler pulse signals each comprised of a burst of a plurality of cycles, means for generating a range gate signal for applying gate signals to said receiving means to enable reception of signals corresponding to said Doppler pulse signals only during predetermined periods following each Doppler pulse signal, means for applying said Doppler pulse signals to said transducer means as said drive signals, said receiving means comprising low pass filter means, said apparatus further comprising means for adjusting the time between each Doppler pulse signal and the respective range gate signal while simultaneously decreasing the cutoff frequency of said low pass filter means for increases in said time and increasing said cutoff frequency for decreases in said time.

6. In an ultrasonic diagnostic apparatus including a transmitting means for generating drive signals, a receiving means for producing output signals for diagnosis, and ultrasound transducer means connected to said transmitting means for emitting ultrasound in response to said drive signals and for applying signals to said receiving means in response to ultrasound echoes responsive to said emitted ultrasound, the improvement wherein said transducer means comprises a transducer, means connecting said transmitting means to said transducer, a narrow band amplifier and a transformer having a primary winding connected to said transducer and a secondary winding connected to said narrow band amplifier, said transformer being tuned to the frequency of emission of said ultrasound.

7. The apparatus of claim 6 wherein said transformer comprises a core that saturates when drive signals are applied to said transducer.

8. The apparatus of claim 6 wherein the coupling between said primary and secondary windings is no greater than critical coupling at the frequency of said ultrasound.

9. In an ultrasonic diagnostic apparatus including a transmitting means for generating drive signals, a receiving means for producing output signals for diagnosis, and ultrasound transducer means connected to said transmitting means for emitting ultrasound in response to said drive signals and for applying echo signals responsive to said emitted ultrasound to said receiving means, and wherein said receiving means comprises means for synchronously demodulating received signals to provide first and second signals demodulated at 90 degrees with respect to one another, the improvement wherein said receiving means further comprises means for peak detecting each of said first and second signals to produce peak detected signals, means for level detecting said peak detected signals to substantially eliminate noise perturbations, phase sensitive full wave pulse generating means connected to said level detecting means, and means for integrating the outputs of said pulse generating means for producing said output signals.

10. In the method of diagnostic analysis employing Doppler pulse generation comprising generating Doppler pulse drive signals in the form of bursts of a plurality of cycles, applying said drive signals to an ultrasound transducer for transmitting bursts of ultrasound, receiving echo ultrasound pulses responsive to said transmitted bursts via said transducer and applying them to a receiving means, generating a range gate signal and displaying the output of said receiving means during the occurrence of said range gate signal; the improvement comprising adjusting the timing between each said burst and the succeeding range gate signal while maintaining the time between each burst and the immediately preceding range gate signal constant and simultaneously adjusting the power of transmitted ultrasound emitted by said transducer in the same sense.

11. In the method of diagnostic analysis employing Doppler pulse generation comprising generating Doppler pulse drive signals in the form of bursts of a plurality of cycles, applying said drive signals to an ultrasound transducer for transmitting bursts of ultrasound, receiving echo ultrasound pulses responsive to said transmitted ultrasound bursts via said transducer and applying them to a receiving means, generating a range gate signal, and displaying the output of said receiving means during the occurrence of said range gate signal; the improvement comprising adjusting the time between each said burst and the succeeding range gate signal and simultaneously adjusting the pulse repetition rate of said bursts while maintaining the time between each burst and the immediately preceding range gate signal substantially constant.

12. The method of claim 11 wherein said step of adjusting comprises varying the time between each range gate signal and the succeeding burst to be only above a determined minimum timing between said bursts and the following range gate signal.

13. In the method of diagnostic analysis employing Doppler pulse generation comprising generating Doppler pulse drive signals in the form of bursts of a plurality of cycles each, applying aid drive signals to an ultrasound transducer for transmitting ultrasound, receiving echo ultrasound pulses responsive to said transmitted ultrasound via said transducer and applying them to a receiving means, generating a range gate signal, and displaying the output of said receiving means in response to said transmitted ultrasound bursts only during the occurrence of said range gate signal; the improvement comprising passing said received signals in said receiving means through a low pass filter, and adjusting the time between each said burst and the succeeding range gate signal and simultaneously adjusting the cut off frequency of said low pass filter whereby the cut off frequency is decreased as said time increases and the cutoff frequency is increased as said time decreases.

14. In the method of diagnostic analysis employing Doppler generation comprising generating ultrasound drive signals, applying said drive signals to an ultrasound transducer for transmitting ultrasound, receiving echo ultrasound signals responsive to said transmitted ultrasound via said transducer and applying them to a receiving means, synchronously demodulating the received signals at 90 degrees to produce quadrature signals, and displaying the output of said receiving means during said range gate signal; the improvement comprising peak detecting said quadrature signals, level detecting the resultant peak detected signals to eliminate noise perturbations, generating pulse signals from said level detected signals in phase sensitive full wave pulse generating means and integrating the full wave generated signals to produce an output signal for diagnostic analysis.

15. In a system for processing continuous signals where said sampling means are provided for sampling said signals at predetermined variable times following a reference time, the sampling means comprising means for producing a gate signal from a leading edge signal that has a timing that is variable with respect to said reference time, the improvement wherein said sampling means comprises means for establishing first and second clock signals of opposite phase for selectively initiating a range gate signal in response to the occurrence of said clock signals, said sampling means comprising means responsive to substantial coincidence between said leading edge and one of said first and second clock signals for initiating said range gate with the other of said clock signals.

16. In an ultrasonic diagnostic apparatus including a transmitting means for generating drive signals, a receiving means for producing output signals for diagnosis, and an ultrasound transducer connected to said transmitting means for emitting ultrasound pulses in response to said drive signals and for applying signals to said receiving means in response to ultrasound pulses received in response to said emitted ultrasound pulses, the improvement wherein said transmitting means comprises means for generating a composite signal comprised of a train of single cycle pulse signals of substantially constant repetition rate each pulse of which is followed by a receiving period and interlaced with a train of Doppler pulse signals, said Doppler pulse signals each being comprised of a plurality of bursts each of a plurality of cycles followed by a receiving period, means for varying the repetition rate of said bursts, and means applying said composite signals as said drive signals to said transducer, and further comprising a narrow-band amplifier connected to said receiving means and means connecting said narrow-band amplifier to said transducer, said narrow-band amplifier having an input impedance critically tuned to reduce Johnson noise and thus provide a substantially improved signal-to-noise ratio at a predetermined frequency.

17. The ultrasonic diagnostic apparatus of claim 16 wherein said connections means comprises a tuned matching transformer having a primary winding coupled to said transducer and a secondary winding coupled to said amplifier.

18. The ultrasonic diagnostic apparatus of claim 17 wherein said transformer has a core that saturates when drive signals are applied to said transducer, the coupling between said primary and secondary windings being no greater than critical at the frequency of said drive signals.

19. In an ultrasonic diagnostic apparatus including a transmitting means for generating drive signals, a receiving means for producing output signals for diagnosis, and an ultrasonic transducer connected to said transmitting means for emitting ultrasonic pulses in response to said drive signals and for applying signals to said receiving means in response to ultrasound pulses received in response to said emitted ultrasound pulses, the improvement wherein said transmitting means comprises means for generating a composite signal comprised of a train of single cycle pulse signals of substantially constant repetition rate each pulse of which is followed by a receiving period and interlaced with a train of Doppler pulse signals, said Doppler pulse signals each being comprised of a plurality of bursts each of a plurality of cycles followed by a receiving period, means for varying the repetition rate of said bursts, and means applying said composite signals as said drive signals to said transducer, said receiving means comprising means for synchronously demodulating received signals to provide first and second signals demodulated at 90 degrees, means for peak detecting each of said first and second signals to produce peak detected signals, means for level detecting said peak detected signals, means for level detecting said peak detected signals to substantially eliminate noise perturbations therefrom, phase-sensitive full-wave pulse generating means connected to said level detecting means, and means for integrating the output of said pulse generating means for producing an output signal.

20. In the method of diagnostic analysis comprising generating drive signals, applying said drive signals to an ultrasound transducer for transmitting ultrasound pulses, receiving echo ultrasound pulses responsive to said transmitted ultrasound pulses via said transducer and applying them to a receiving means, and displaying the output of said receiving means; the improvement wherein said step of generating drive signals comprises generating a composite drive signal comprised of a train of single cycle pulse signals of constant repetition rate each followed by a receive time and interlaced with a train of Doppler pulse signals, said Doppler pulse signals, each being comprised of a plurality of bursts of a plurality of cycles followed by a receive period, further comprising varying the repetition rate of said bursts, and said step of applying comprises applying said composite drive signal to said transducer, and further comprising the steps of synchronously demodulating received signals at 90 degrees to produce quadrature signals, peak detecting said quadrature signal level detecting the resultant peak detected signals to eliminate noise perturbations, generating pulse signals from said level detected signals in phase-sensitive full-wave pulse generating means, and integrating the generated pulse signals to produce an output signal.

21. In an ultrasonic diagnostic apparatus, including transmitting means for generating drive signals, receiving means for producing output signals for diagnosis, and an ultrasound transducer connected to said transmitting means for emitting ultrasound pulses in response to said drive signals and for applying signals to said receiving means in response to ultrasound pulses received in response to said emitted ultrasound pulses, the improvement wherein said receiving means comprises means for synchronously demodulating received signals to provide first and second signals demodulated at 90°, means for peak detecting each of said first and second signals to produce peak detected signals, means, and means or integrating the output of said pulse generating means for producing an output signal.

22. In the method of diagnostic analysis comprising generating drive signals, applying said drive signals to an ultrasound transducer for transmitting ultrasound pulses, receiving echo ultrasound pulses responsive to said transmitted ultrasound pulses via said transducer and applying them to a receiving means, and displaying the output of said receiving means, the improvement comprising synchronously demodulating signals received by said receiving means at 90° to produce quadrature signal, peak detecting said quadrature signals, level detecting the resultant peak detected signals to eliminate noise perturbations, generating pulse signals from said level detected signals in phase-sensitive full-wave pulse generating means, and integrating the generated pulse signals to produce an output signal.

23. In a ultrasonic diagnostic apparatus, including a transmitting means for generating drive signals, a receiving means for producing output signals for diagnosis, an ultrasound transducer means connected to said transmitting means for emitting ultrasound pulses in response to said drive signals and for applying signals to said receiving means in response to ultrasound pulses received in response to said emitted ultrasound pulses, the improvement wherein said transmitting means comprises means for generating a train of Doppler pulse signals, each comprised of a burst of plurality of cycles followed by a receiving cycle, and means for generating a range gate signal for applying gate signals to said receiving means to enable reception of signals by said receiving means corresponding to said Doppler pulse signals only during predetermined periods following each Doppler pulse signal, means for applying said Doppler signals to said transducer means as said drive signals, and means for adjusting the time between each Doppler pulse signal and the respective range gate signal, said means for generating a range gate signal comprising means for establishing first and second clock signals of opposite phase, and means responsive to substantial coincidence between the leading edge of said range gate signal and one of said first and second clock signals for initiating said range gate signal with the other of said clock signals, aid one clock signal being that one of said clock signals that initiated the last previous range gate signal.

* * * * *